United States Patent
Akao et al.

(10) Patent No.: US 11,041,152 B2
(45) Date of Patent: Jun. 22, 2021

(54) MICRORNA-143 DERIVATIVE

(71) Applicants: e-NA Biotec Inc., Gifu (JP); Yukihiro Akao, Gifu (JP); Yukio Kitade, Aichi (JP)

(72) Inventors: Yukihiro Akao, Gifu (JP); Yukio Kitade, Aichi (JP); Mitsuaki Sekiguchi, Osaka (JP); Yasunori Mitsuoka, Osaka (JP); Akira Kugimiya, Osaka (JP); Yasuo Sasaki, Osaka (JP)

(73) Assignees: E-NA BIOTEC INC., Gifu (JP); Yukihiro Akao, Gifu (JP); Yukio Kitade, Aichi (JP)

( * ) Notice: Subject to any disclaimer, the term of this patent is extended or adjusted under 35 U.S.C. 154(b) by 0 days.

(21) Appl. No.: 16/092,830

(22) PCT Filed: Apr. 13, 2017

(86) PCT No.: PCT/JP2017/015153
§ 371 (c)(1),
(2) Date: Oct. 11, 2018

(87) PCT Pub. No.: WO2017/179660
PCT Pub. Date: Oct. 19, 2017

(65) Prior Publication Data
US 2019/0119677 A1    Apr. 25, 2019

(30) Foreign Application Priority Data
Apr. 14, 2016 (JP) .............................. JP2016-081253

(51) Int. Cl.
| *C12N 15/113* | (2010.01) |
| *C12N 15/09* | (2006.01) |
| *A61K 48/00* | (2006.01) |
| *A61K 31/713* | (2006.01) |
| *A61P 35/00* | (2006.01) |
| *C07H 21/02* | (2006.01) |

(52) U.S. Cl.
CPC .......... *C12N 15/113* (2013.01); *A61K 31/713* (2013.01); *A61K 48/00* (2013.01); *A61P 35/00* (2018.01); *C07H 21/02* (2013.01); *C12N 15/09* (2013.01); *A61K 48/0066* (2013.01); *C12N 2310/141* (2013.01)

(58) Field of Classification Search
CPC ............ C12N 15/113; C12N 2310/141; C12N 2310/322
See application file for complete search history.

(56) References Cited

U.S. PATENT DOCUMENTS

| 2010/0234451 A1* | 9/2010 | Worm ........................ A61P 5/26 |
| | | 514/44 R |
| 2012/0093789 A1* | 4/2012 | Srivastava ........... C12N 5/0691 |
| | | 424/93.21 |
| 2014/0315982 A1 | 10/2014 | Tachibana et al. |

FOREIGN PATENT DOCUMENTS

| EP | 2 774 989 | 9/2014 |
| JP | 2008-86201 | 4/2008 |
| JP | 2011-251912 | 12/2011 |
| WO | 2010/032704 | 3/2010 |
| WO | 2013/065791 | 5/2013 |

OTHER PUBLICATIONS

MiRBase: the microRNA database MI0000459 Hsa-mir-143, pp. 1-3 retrieved on the line Sep. 23, 2020, http://www.mirbase.org/cgi-bin/mirna_entry.pl?acc=MI0000459 (Year: 2018).*
English translation of WO 2010/032704A1, pp. 1-36, retrieved on Oct. 2, 2020 (Year: 2010).*
Notice of Reason for Refusal dated Mar. 3, 2020 in corresponding Japanese Patent Application No. 2018-512071 with English-language translation.
International Preliminary Report on Patentability dated Oct. 25, 2018 in International Application No. PCT/JP2017/015153.
Extended European Search Report dated Nov. 18, 2019 in corresponding European Patent Application No. 17782473.7.
International Search Report (ISR) dated Jun. 27, 2017 in International (PCT) Application No. PCT/JP2017/015153.
Yukihiro Akao et al., "MicroRNAs 143 and 145 are possible common onco-microRNAs in human cancers", Oncology Reports, 16, pp. 845-850, 2006.
Y. Akao et al., "Role of anti-oncomirs miR-143 and -145 in human colorectal tumors", Cancer Gene Therapy, 17, pp. 398-408, 2010.
Syunsuke Noguchi et al., "MicroRNA-143 functions as a tumor suppressor in human bladder cancer T24 cells", Cancer Letters, 307, pp. 211-220, 2011.
Yukihiro Akao et al., "Downregulation of microRNAs-143 and -145 in B-cell malignancies", Cancer Science, 98, pp. 1914-1920, 2007.
Yoshiaki Kitamura et al., "Chemically modified siRNAs and miRNAs bearing urea/thiourea-bridged aromatic compounds at their 3'-end for RNAi therapy", Bioorganic & Medicinal Chemistry, 21, pp. 4494-4501, 2013.

* cited by examiner

*Primary Examiner* — Brian Whiteman
(74) *Attorney, Agent, or Firm* — Wenderoth, Lind & Ponack, L.L.P.

(57) ABSTRACT

The purpose of the present invention is to provide novel miR-143 derivatives described herein that can be used as oligonucleotide therapeutics.

2 Claims, 5 Drawing Sheets
Specification includes a Sequence Listing.

[Fig. 1]
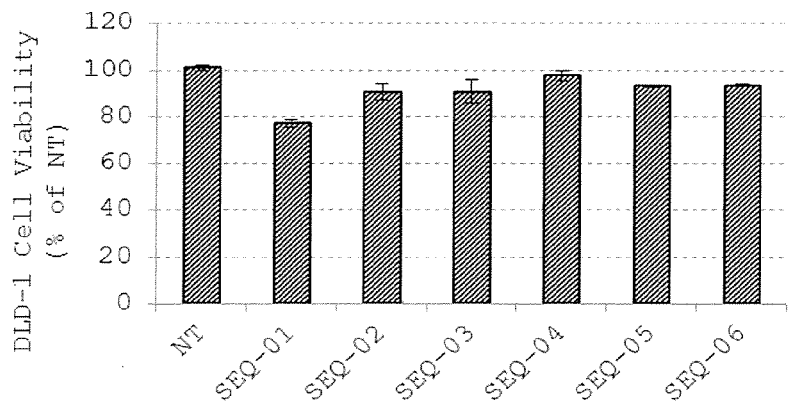
[Fig. 2]
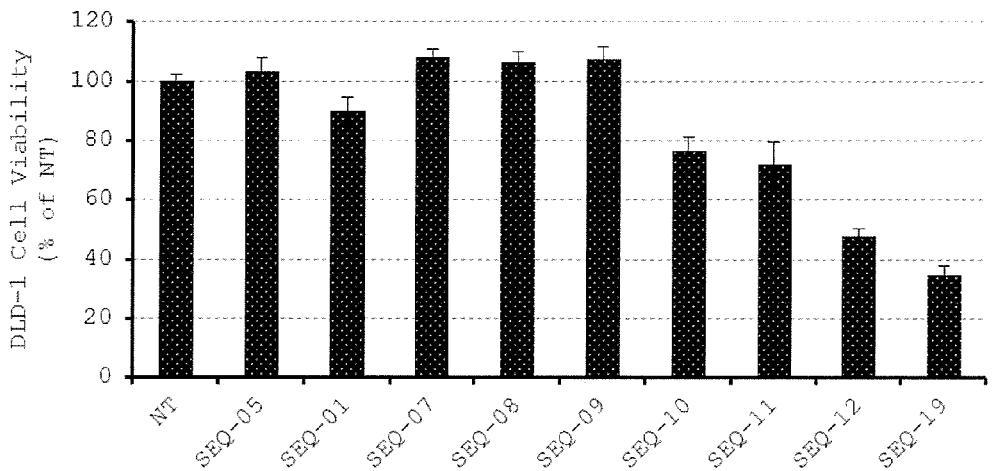
[Fig. 3]
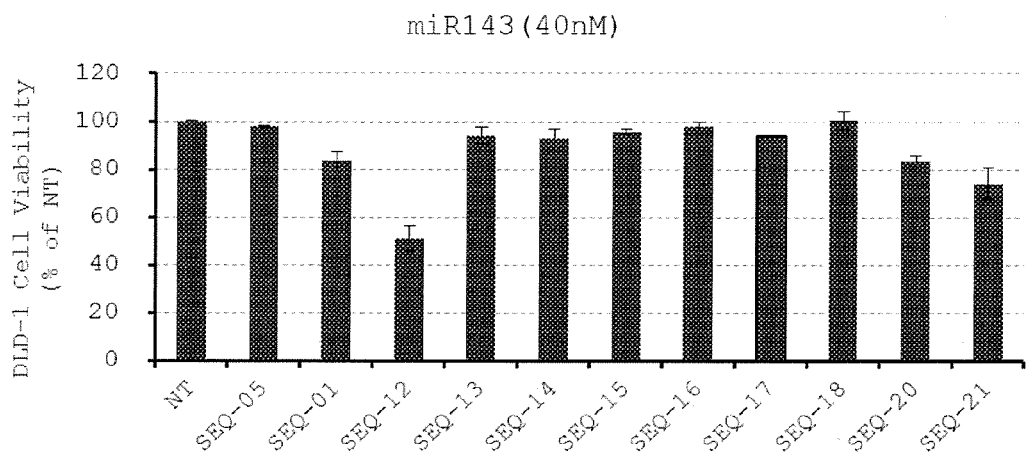

[Fig. 4]
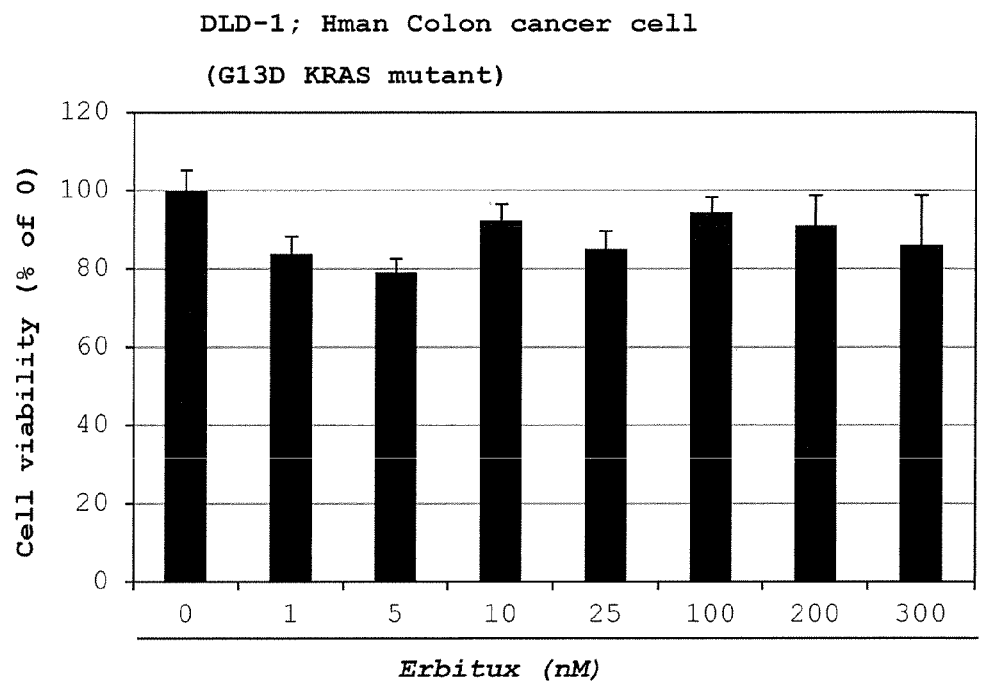
[Fig. 5]
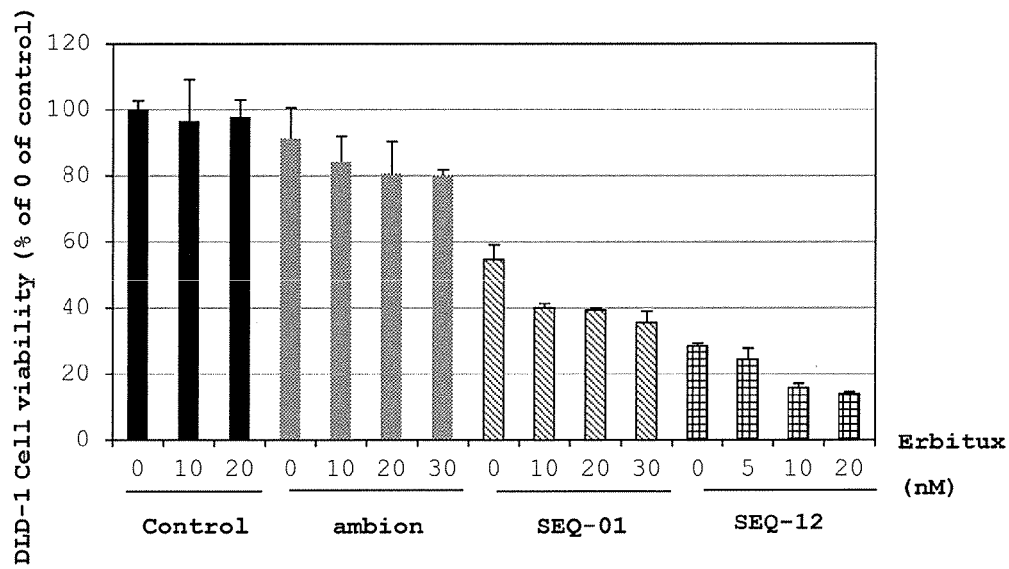

[Fig. 6]
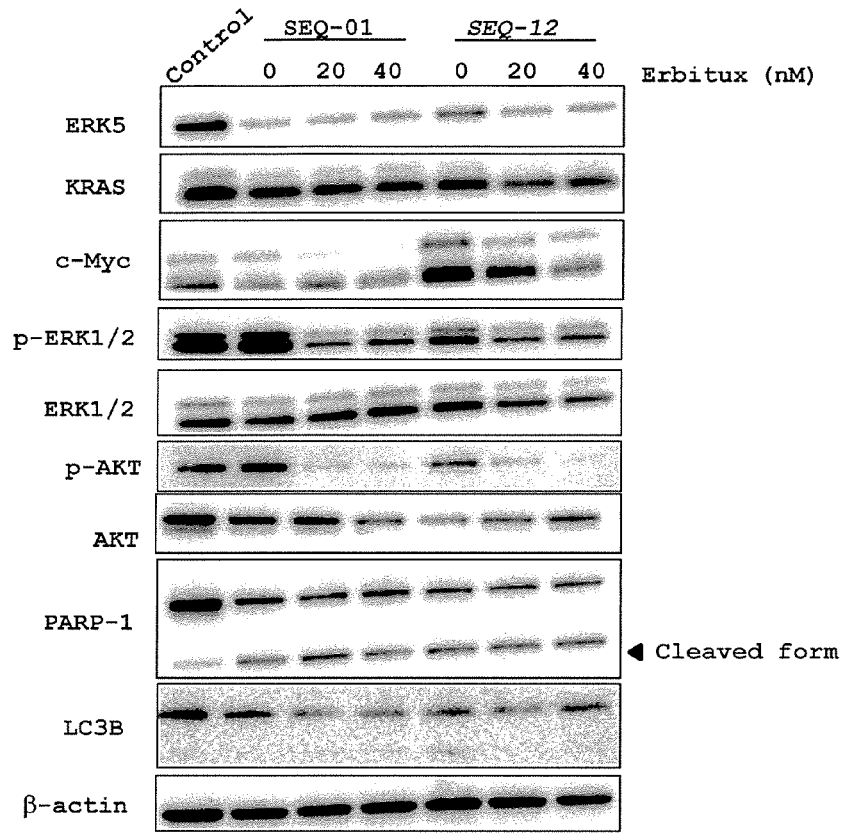
[Fig. 7]
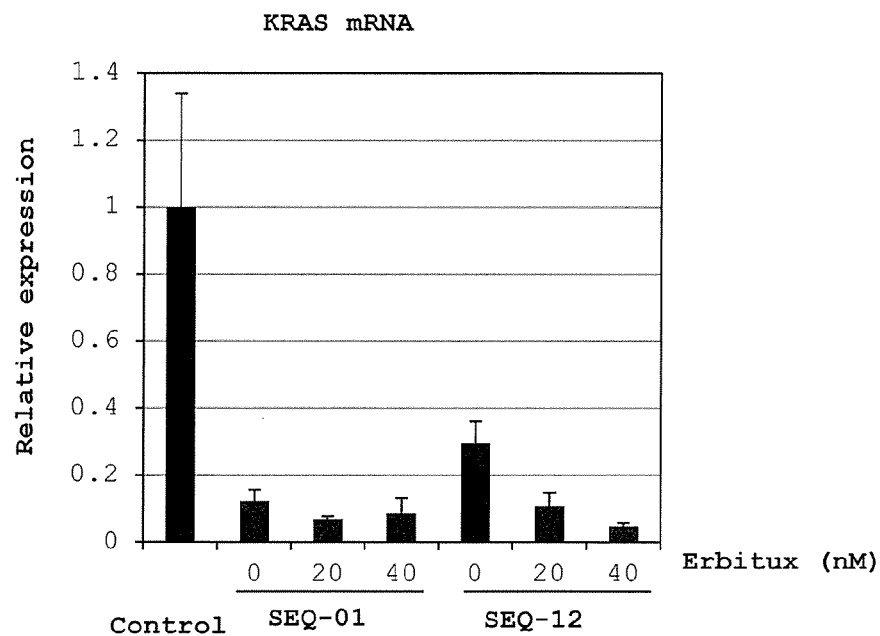

[Fig. 8]
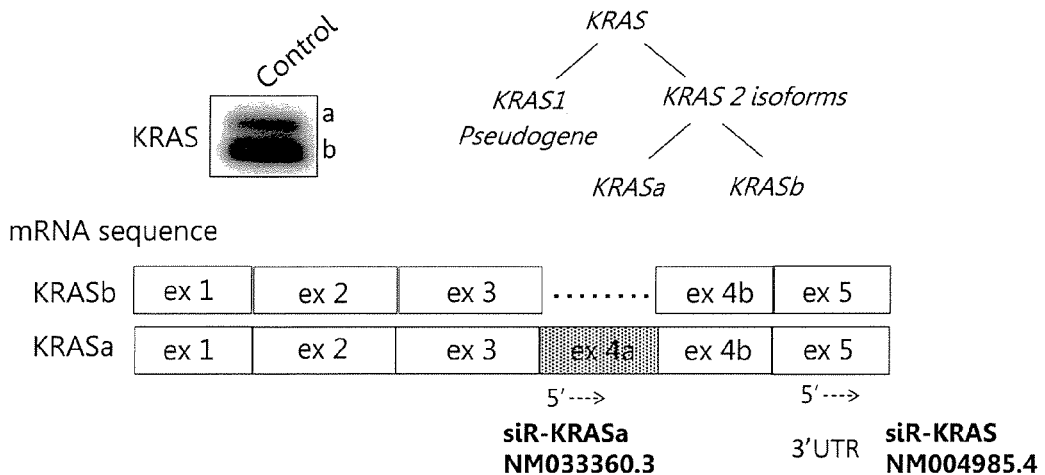
[Fig. 9]
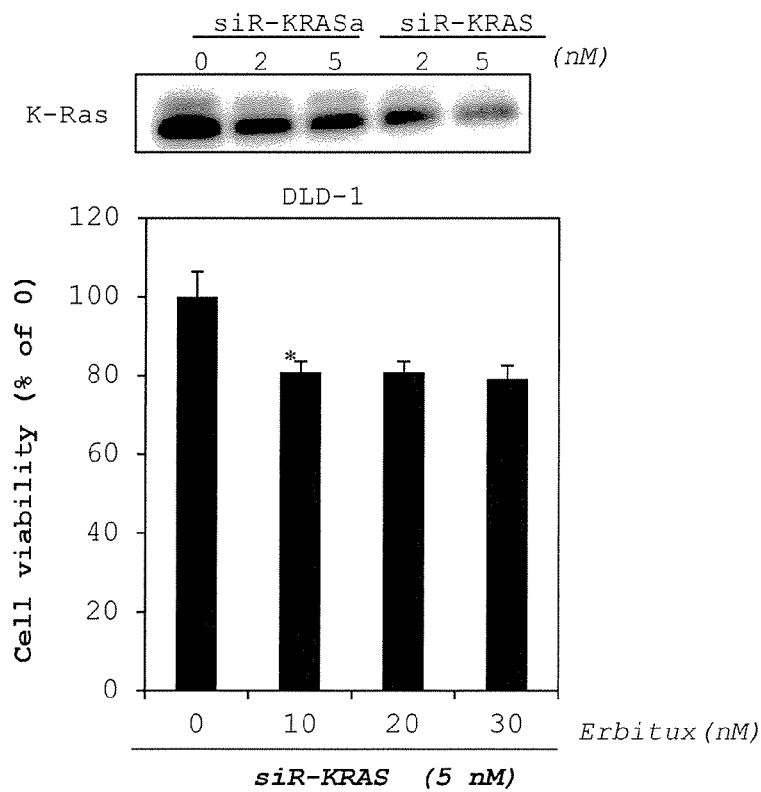

[Fig. 10]
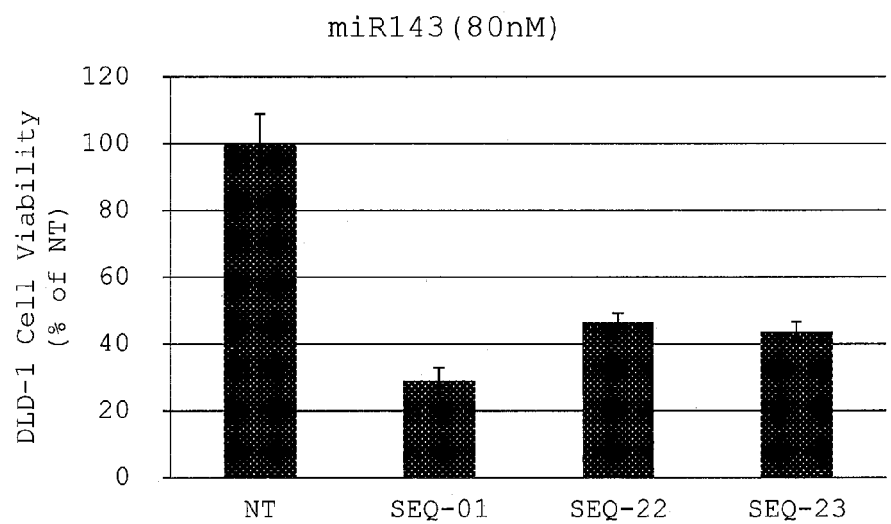
[Fig. 11]
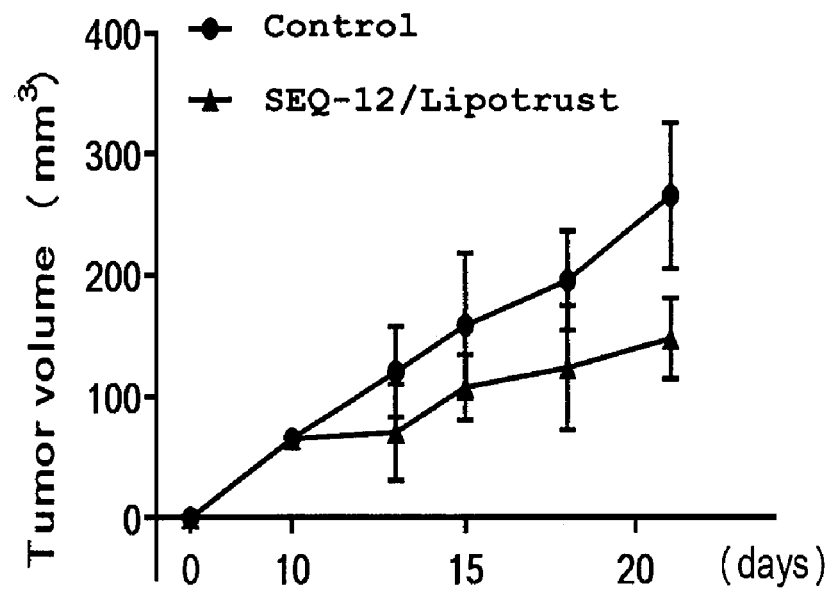

SEQUENCE LISTING

<160> NUMBER OF SEQ ID NOS: 24

<210> SEQ ID NO 1
<211> LENGTH: 22
<212> TYPE: RNA
<213> ORGANISM: Homo sapiens

<400> SEQUENCE: 1
ggugcagugc ugcaucucug gu        22

<210> SEQ ID NO 2
<211> LENGTH: 21
<212> TYPE: RNA
<213> ORGANISM: Homo sapiens

<400> SEQUENCE: 2
ugagaugaag cacuguagcu c        21

<210> SEQ ID NO 3
<211> LENGTH: 24
<212> TYPE: RNA
<213> ORGANISM: Artificial sequence
<220> FEATURE:
<223> OTHER INFORMATION: Passenger strand of miR143 derivative

<400> SEQUENCE: 3
ugaggugcag ugcugcaucu cugg        24

<210> SEQ ID NO 4
<211> LENGTH: 22
<212> TYPE: RNA
<213> ORGANISM: Artificial sequence
<220> FEATURE:
<223> OTHER INFORMATION: Guide sequence of miR143 derivative

<400> SEQUENCE: 4
ugagaugaag cacuguagcu ca        22

<210> SEQ ID NO 5
<211> LENGTH: 24
<212> TYPE: RNA
<213> ORGANISM: Artificial sequence
<220> FEATURE:
<223> OTHER INFORMATION: Guide sequence of miR-143

<400> SEQUENCE: 5
ugagaugaag cacuguagcu cagg        24

<210> SEQ ID NO 6
<211> LENGTH: 22
<212> TYPE: RNA
<213> ORGANISM: Artificial sequence
<220> FEATURE:
<223> OTHER INFORMATION: Passenger strand of miR143 derivative

<400> SEQUENCE: 6
ugagcuacag ugcugcaucu cu                                              22

<210> SEQ ID NO 7
<211> LENGTH: 19
<212> TYPE: RNA
<213> ORGANISM: Artificial sequence
<220> FEATURE:
<223> OTHER INFORMATION: Passenger strand of miR143 derivative

<400> SEQUENCE: 7
ugaggaguag ugaaaggcc                                                  19

<210> SEQ ID NO 8
<211> LENGTH: 19
<212> TYPE: RNA
<213> ORGANISM: Artificial sequence
<220> FEATURE:
<223> OTHER INFORMATION: Guide sequence of miR143 derivative

<400> SEQUENCE: 8
ggccuuucac uacuccuca                                                  19

<210> SEQ ID NO 9
<211> LENGTH: 22
<212> TYPE: RNA
<213> ORGANISM: Artificial sequence
<220> FEATURE:
<223> OTHER INFORMATION: Passenger strand of miR143 derivative

<400> SEQUENCE: 9
ugaggugcag ugcugcaucu cu                                              22

<210> SEQ ID NO 10
<211> LENGTH: 25
<212> TYPE: RNA
<213> ORGANISM: Artificial sequence
<220> FEATURE:
<223> OTHER INFORMATION: siRNA for KRAS (3'UTR)

<400> SEQUENCE: 10
aaugcaugac aacacuggau gaccg                                           25

<210> SEQ ID NO 11
<211> LENGTH: 25
<212> TYPE: RNA
<213> ORGANISM: Artificial sequence
<220> FEATURE:
<223> OTHER INFORMATION: siRNA for KRASa (ORF)

<400> SEQUENCE: 11
uauugucgga ucucccucac caaug                                           25

<210> SEQ ID NO 12
<211> LENGTH: 21
<212> TYPE: RNA
<213> ORGANISM: Artificial sequence
<220> FEATURE:
<223> OTHER INFORMATION: Passenger strand of miR143 derivative

<400> SEQUENCE: 12
ggugcagugc ugcaucucug g                                               21

<210> SEQ ID NO 13
<211> LENGTH: 19

```
<212> TYPE: RNA
<213> ORGANISM: Artificial sequence
<220> FEATURE:
<223> OTHER INFORMATION: Guide sequence of miR143 derivative

<400> SEQUENCE: 13
ugagaugaag cacuguagc                                                   19

<210> SEQ ID NO 14
<211> LENGTH: 24
<212> TYPE: RNA
<213> ORGANISM: Artificial sequence
<220> FEATURE:
<223> OTHER INFORMATION: Passenger strand of miR143 derivative

<400> SEQUENCE: 14
ugagcugcag ugcugcaucu cugg                                             24

<210> SEQ ID NO 15
<211> LENGTH: 24
<212> TYPE: RNA
<213> ORGANISM: Artificial sequence
<220> FEATURE:
<223> OTHER INFORMATION: Passenger strand of miR143 derivative

<400> SEQUENCE: 15
ugagguacag ugcugcaucu cugg                                             24

<210> SEQ ID NO 16
<211> LENGTH: 24
<212> TYPE: RNA
<213> ORGANISM: Artificial sequence
<220> FEATURE:
<223> OTHER INFORMATION: Passenger strand of miR143 derivative

<400> SEQUENCE: 16
ugagcugcag ugcugcaucu cugg                                             24

<210> SEQ ID NO 17
<211> LENGTH: 24
<212> TYPE: RNA
<213> ORGANISM: Artificial sequence
<220> FEATURE:
<223> OTHER INFORMATION: Passenger strand of miR143 derivative

<400> SEQUENCE: 17
ugaggugcag ugcugcaucu cagg                                             24

<210> SEQ ID NO 18
<211> LENGTH: 20
<212> TYPE: RNA
<213> ORGANISM: Artificial sequence
<220> FEATURE:
<223> OTHER INFORMATION: Guide sequence of miR143 derivative

<400> SEQUENCE: 18
ugagaugaag cacuguagcu                                                  20

<210> SEQ ID NO 19
<211> LENGTH: 24
<212> TYPE: RNA
<213> ORGANISM: Artificial sequence
<220> FEATURE:
<223> OTHER INFORMATION: Passenger strand of miR143 derivative

<400> SEQUENCE: 19
```

```
cgaggugcag ugcugcaucu cugg                                          24

<210> SEQ ID NO 20
<211> LENGTH: 24
<212> TYPE: DNA
<213> ORGANISM: Artificial sequence
<220> FEATURE:
<223> OTHER INFORMATION: Passenger strand of miR143 derivative

<400> SEQUENCE: 20
tgaggugcag ugcugcaucu cugg                                          24

<210> SEQ ID NO 21
<211> LENGTH: 23
<212> TYPE: RNA
<213> ORGANISM: Artificial sequence
<220> FEATURE:
<223> OTHER INFORMATION: Passenger strand of miR143 derivative

<400> SEQUENCE: 21
gaggugcagu gcugcaucuc ugg                                           23

<210> SEQ ID NO 22
<211> LENGTH: 23
<212> TYPE: RNA
<213> ORGANISM: Artificial sequence
<220> FEATURE:
<223> OTHER INFORMATION: Passenger strand of miR143 derivative

<400> SEQUENCE: 22
ugaggugcag ugcugcaucu cgg                                           23

<210> SEQ ID NO 23
<211> LENGTH: 19
<212> TYPE: RNA
<213> ORGANISM: Artificial sequence
<220> FEATURE:
<223> OTHER INFORMATION: 1st strand of Control dsRNA

<400> SEQUENCE: 23
guaggaguag ugaaaggcc                                                19

<210> SEQ ID NO 24
<211> LENGTH: 19
<212> TYPE: RNA
<213> ORGANISM: Artificial sequence
<220> FEATURE:
<223> OTHER INFORMATION: 2nd strand of Control dsRNA

<400> SEQUENCE: 24
ggccuuucac uacuccuac                                                19
```

MICRORNA-143 DERIVATIVE

FIELD OF THE INVENTION

The present invention relates to new microRNA-143 derivatives (hereinafter referred to as "miR-143"). It also relates to pharmaceutical compositions comprising the miR-143 derivative. Furthermore, it relates to combinations of the miR-143 derivative and an EGFR inhibitor.

BACKGROUND ART

MicroRNA (hereinafter referred to as "miRNA") is an endogenous, non-coding RNA of about 20 to 25 bases encoded on the genome. miRNA is transcribed from a miRNA gene on the genomic DNA first as a primary transcript (Primary miRNA, Pri-miRNA) having a length of about several hundred to several thousand bases, and then processed into a pre-miRNA (precursor miRNA) having a hairpin structure of about 60 to 110 bases. Thereafter, it moves from the nucleus into the cytoplasm and is further spliced into a double-stranded miRNA of about 20 to 25 bases. The double-stranded miRNA is incorporated into a protein called RISC to be a single-stranded miRNA (the guide strand, antisense strand), and then the more unstable single strand (the passenger strand, sense strand) is degraded. The single-stranded miRNA binds to mRNA of the target gene having a partially complementary base sequence and inhibit translation of the target gene.

There are 1000 or more kinds of miRNAs known for human, mouse and the like, each of which is suggested to regulate expression of plural target genes, and be involved in various life phenomena such as growth and differentiation of the cell and onset and progression of cancers, cardiovascular diseases, neurodegenerative diseases, mental disorders, chronic inflammatory diseases and the like. Especially, many researchers have pointed out that miRNAs are deeply involved in cancer cell growth, and therefore the miRNAs have been researched and developed as oligonucleotide therapeutics.

miR-143 is one of the miRNAs which is suggested the relationship with cancer. Non-patent Document 1 discloses that miR-143 inhibits the proliferation of colon cancer cells (DLD-1, SW480) (see FIG. 3). In addition, Patent Document 1 and Non-patent Document 2 and 3 disclose that a derivative wherein at least one to three portions in the sense strand of four mismatched portions of miR-143 were matched, and 3'-ends of the sense strand and antisense strand were modified with benzene-pyridine derivatives (BP), has excellent growth inhibitory effect on cancer cells compared to wild-type miR-143.

PRIOR ART DOCUMENT

Patent Document

Patent Document 1: WO2010/032704

Non-Patent Document

Non-patent Document 1: Oncology Report, 16, 845-850 (2006)
Non-patent Document 2: Cancer Gene Therapy, 17, 398-408 (2010)
Non-patent Document 3: Cancer Letters, 307, 211-220 (2011)

SUMMARY OF THE INVENTION

Problems to be Solved by the Invention

The purpose of the present invention is to provide new miR-143 derivatives which are useful as oligonucleotide therapeutics.

Means for Solving the Problem

The present inventors have intensively studied and found that a miR-143 derivative of the present invention wherein the first strand is a sequence of SEQ ID NO: 3 and the second strand is a sequence of SEQ ID NO: 5 (SEQ-01 in Examples) has stronger tumor growth inhibitory effect than SEQ-22 that the sense strand (the first strand) is one base shorter at the 3'-end and the antisense strand (the second strand) is same compared to the wild type (wild-type human miR-143 consisting of SEQ ID NO: 1 and 2) (FIG. 10). Furthermore, they found that SEQ-01 has stronger tumor growth inhibitory effect than SEQ-23 that two bases at the 3'-end of the second strand of SEQ-22 were deleted and a 3'-end modification (^dT^dT) was introduced (FIG. 10).

In addition, they found that miR-143 derivatives of the present invention wherein the first strand is a sequence of SEQ ID NO: 3 and does not include a 3'-end modification, and the second strand is SEQ ID NO: 4 (that is, two bases at the 3'-end of the second strand of SEQ-01 were deleted) and includes a 3'-end modification (SEQ-10 to 12, 19 to 21, 24 to 144 in Examples) showed better tumor growth inhibitory effect than SEQ-01 and excellent growth inhibitory effect on cancer cells compared to wild-type miR-143 or the other miR-143 derivatives (SEQ-02 to 04, 07 to 09 and 13 to 18 in Examples) (FIG. 1 to 3, Table 13). miR-143 derivatives of the present invention are very useful as oligonucleotide therapeutics, especially medicines for treating cancers or suppressing the exacerbation thereof.

Furthermore, the present inventors found that combinations of cetuximab which is an EGFR inhibitor and a miR-143 derivative of the present invention (SEQ-01 or SEQ-12) have anti-tumor effect even for KRAS mutant cancer (FIGS. 4 and 5). It is thought that there is a high possibility that EGFR inhibitors are not expected to have pharmacological effects in the presence of KRAS mutation. For example, in the Japanese package insert for Erbitux (registered trademark) which is a formulation comprising cetuximab, the indication is "EGFR-positive, progressive or recurrent colorectal cancer or head and neck cancer that is refractory and inoperable" and the note, "Select applicable patients considering the presence or absence of RAS (KRAS and NRAS) gene mutations", was described. The miR-143 derivatives of the present invention are very useful because an EGFR inhibitor can be administered by combining the EGFR inhibitor and a miR-143 derivative of the present invention to the patients that the administration of the EGFR inhibitor has been difficult.

That is, the present invention is related to the followings.
(I-1) A microRNA-143 derivative, wherein
the first strand is an oligonucleotide consisting of
a sequence of SEQ ID NO: 3 or
a sequence in which one or two bases are substituted, deleted, inserted or added to the sequence of SEQ ID NO: 3 and
does not include a 3'-end modification, but may include a 5'-end modification; and the second strand is an oligonucleotide consisting of a sequence of SEQ ID NO: 4 or
a sequence in which one or two bases are substituted, deleted or inserted to the sequence of SEQ ID NO: 4 and
includes a 3'-end modification, and may include a 5'-end modification;
or
a sequence of SEQ ID NO: 5 or
a sequence in which one or two bases are substituted or inserted to the sequence of SEQ ID NO: 5 and
does not include a 3'-end modification, and may include a 5'-end modification;
wherein
the 3'-end modification is a 1 to 5-mer oligonucleotide derivative which may include a nucleoside derivative(s) and/or modified internucleoside linkage(s) or a benzene-pyridine derivative and
the 5'-end modification is a phosphate ester moiety or a group of the formula: =CQ$_1$-P(=O)(OH)$_2$, wherein Q$_1$ is hydrogen, halogen, substituted or unsubstituted alkyl, substituted or unsubstituted alkenyl, substituted or unsubstituted alkynyl, or substituted or unsubstituted alkyloxy.

(I-2) The microRNA-143 derivative of (I-1), wherein
the first strand is an oligonucleotide consisting of a sequence of SEQ ID NO: 3 and
the second strand is an oligonucleotide consisting of a sequence of SEQ ID NO: 4 or 5.

(I-3) The microRNA-143 derivative of (I-1) or (I-2), wherein the oligonucleotide derivative is 1 or 2-mer.

(I-4) The microRNA-143 derivative of any one of (I-1) to (I-3), wherein the nucleoside derivative is a nucleoside having a substituent at the 2' position of the sugar moiety or a nucleoside having a bridged structure between the 4' and 2' positions of the sugar moiety.

(I-5) The microRNA-143 derivative of (I-4), wherein the substituent is F, OCH$_3$ or OCH$_2$CH$_2$OCH$_3$.

(I-6) The microRNA-143 derivative of (I-4), wherein the bridged structure is 4'-(CH$_2$)m-O-2', wherein m is an integer of 1 to 4, or 4'-C(=O)—NR$^3$-2', wherein R$^3$ is a hydrogen atom or alkyl.

(I-7) The microRNA-143 derivative of any one of (I-1) to (I-6), wherein the modified internucleoside linkage is a phosphorothioate linkage.

(I-8) The microRNA-143 derivative of (I-1) selected from the group of consisting of SEQ-12, SEQ-19, SEQ-29, SEQ-51, SEQ-52, SEQ-56, SEQ-60, SEQ-73, SEQ-74, SEQ-86, SEQ-89, SEQ-94, SEQ-106, SEQ-122, SEQ-123, SEQ-124, SEQ-127, SEQ-139, SEQ-140, SEQ-141, SEQ-142, SEQ-143 and SEQ-144.

(I-9) A pharmaceutical composition comprising the microRNA-143 derivative of any one of (I-1) to (I-8).

(I-10) A medicine comprising a combination of the microRNA-143 derivative of any one of (I-1) to (I-8) and an EGFR inhibitor.

(I-11) The medicine of (I-10) which is a combination drug.

(I-12) The medicine of (I-10) characterized by using in combination of the microRNA-143 derivative of any one of (I-1) to (I-8) and an EGFR inhibitor.

(I-13) The medicine of (I-12) characterized by administering simultaneously or sequentially the microRNA-143 derivative of any one of (I-1) to (I-8) and an EGFR inhibitor.

(I-14) The medicine of (I-12) characterized by administering the microRNA-143 derivative of any one of (I-1) to (I-8) and an EGFR inhibitor separately.

(I-15) The medicine of any one of (I-10) to (I-14), wherein the EGFR inhibitor is cetuximab.

(I-16) The medicine of any one of (I-10) to (I-15) for treating cancer or suppressing the exacerbation thereof.

(I-17) A medical agent to enhance the therapeutic effect on cancer of an EGFR inhibitor comprising the microRNA-143 derivative of any one of (I-1) to (I-8).

(I-18) A medical agent to enhance the therapeutic effect on cancer of the microRNA-143 derivative of any one of (I-1) to (I-8) comprising an EGFR inhibitor.

(I-19) A pharmaceutical composition comprising the microRNA-143 derivative of any one of (I-1) to (I-8) as an active ingredient to use in combination with an EGFR inhibitor.

(I-20) A pharmaceutical composition comprising an EGFR inhibitor as an active ingredient to use in combination with the microRNA-143 derivative of any one of (I-1) to (I-8).

(I-21) The pharmaceutical composition of (I-19) or (I-20) for treating cancer or suppressing the exacerbation thereof.

In addition, the present invention includes the followings.

(II-1) A microRNA-143 derivative wherein
the first strand is an RNA oligonucleotide wherein the internucleoside linkages are phosphodiester bonds, and
the second strand is an oligonucleotide comprising a nucleoside derivative(s) and/or a modified internucleoside linkage(s),
wherein a group of the formula: dX$^1$dX$^2$, wherein X$^1$ and X$^2$ are each independently A, G, C or T, or a benzene-pyridine derivative is bound to the 3'-end of the second strand.

(II-2) The microRNA-143 derivative of (II-1), wherein the nucleoside derivative is a nucleoside having a substituent at the 2' position of the sugar moiety and/or a nucleoside having a bridged structure between the 4' and 2' positions of the sugar moiety.

(II-3) The microRNA-143 derivative of (II-2), wherein the substituent is F, OCH$_3$ or OCH$_2$ CH$_2$ OCH$_3$.

(II-4) The microRNA-143 derivative of (II-2), wherein the bridged structure is 4'-(CH$_2$)m-O-2', wherein m is an integer of 1 to 4, or 4'-C(=O)—NR$^3$-2', wherein R$^3$ is a hydrogen atom or alkyl.

(II-5) The microRNA-143 derivative of any one of (II-1) to (II-4), wherein the modified internucleoside linkage is a phosphorothioate linkage.

(II-6) The microRNA-143 derivative of any one of (II-1) to (II-5), wherein a phosphate ester moiety is bound to the 5'-end of the second strand.

(II-7) The microRNA-143 derivative of any one of (II-1) to (II-6), wherein X$^1$ and X$^2$ are T.

(II-8) The microRNA-143 derivative of any one of (II-1) to (II-7),
the first strand is an oligonucleotide less than 30 bases comprising
a sequence of SEQ ID NO: 1 or 3 or
a sequence in which one or several bases are substituted, inserted, deleted and/or added to the sequence of SEQ ID NO: 1 or 3; and
the second strand is an oligonucleotide less than 30 bases comprising a sequence of SEQ ID NO: 2 or 4 or
a sequence in which one or several bases are substituted, inserted, deleted and/or added to the sequence of SEQ ID NO: 2 or 4.

(II-9) The microRNA-143 derivative of (II-8), wherein
the first strand is an oligonucleotide consisting of a sequence of SEQ ID NO: 3 and
the second strand is an oligonucleotide consisting of a sequence of SEQ ID NO: 4.

(II-10) A pharmaceutical composition comprising the microRNA-143 derivative of any one of (II-1) to (II-9).
(II-11) A microRNA-143 derivative wherein
the first strand is an oligonucleotide consisting of a sequence of SEQ ID NO: 3 and
the second strand is an oligonucleotide consisting of a sequence of SEQ ID NO: 5.
(II-12) A pharmaceutical composition comprising the microRNA-143 derivative of (II-11).
(II-13) A medicine comprising a combination of the microRNA-143 derivative of any one of (II-1) to (II-9) and (II-11) and an EGFR inhibitor.
(II-14) The medicine of (II-13) which is a combination drug.
(II-15) The medicine of (II-13) characterized by using in combination of the microRNA-143 derivative of any one of (II-1) to (II-9) and (II-11) and an EGFR inhibitor.
(II-16) The medicine of (II-15) characterized by administering simultaneously or sequentially the microRNA-143 derivative of any one of (II-1) to (II-9) and (II-11) and an EGFR inhibitor.
(II-17) The medicine of (II-15) characterized by administering the microRNA-143 derivative of any one of (II-1) to (II-9) and (II-11) and an EGFR inhibitor separately.
(II-18) The medicine of any one of (II-13) to (II-17), wherein the EGFR inhibitor is cetuximab.
(II-19) The medicine of any one of (II-13) to (II-18) for treating cancer or suppressing the exacerbation thereof.
(II-20) A medical agent to enhance the therapeutic effect on cancer of an EGFR inhibitor comprising the microRNA-143 derivative of any one of (II-1) to (II-9) and (II-11).
(II-21) A medical agent to enhance the therapeutic effect on cancer of the microRNA-143 derivative of any one of (II-1) to (II-9) and (II-11) comprising an EGFR inhibitor.
(II-22) A pharmaceutical composition comprising the microRNA-143 derivative of any one of (II-1) to (II-9) and (II-11) as an active ingredient to use in combination with an EGFR inhibitor.
(II-23) A pharmaceutical composition comprising an EGFR inhibitor as an active ingredient to use in combination with the microRNA-143 derivative of any one of (II-1) to (II-9) and (II-11).
(II-24) The pharmaceutical composition of (II-22) or (II-23) for treating cancer or suppressing the exacerbation thereof.

Effect of the Invention miR-143 derivatives of the present invention show excellent growth inhibitory effect on cells, and are very useful as a medicine for treating cancer or suppressing the exacerbation thereof. Furthermore, combinations of a miR-143 derivative of the present invention and an EGFR inhibitor are very useful as a medicine especially for treating KRAS mutant cancer that administration of an EGFR inhibitor is difficult or suppressing the exacerbation thereof.

BRIEF DESCRIPTION OF THE DRAWINGS

FIG. 1 Tumor growth inhibitory effect of miR-143 derivatives on DLD-1 cells
FIG. 2 Tumor growth inhibitory effect of miR-143 derivatives on DLD-1 cells
FIG. 3 Tumor growth inhibitory effect of miR-143 derivatives on DLD-1 cells
FIG. 4 Tumor growth inhibitory effect of an anti-EGFR antibody (Erbitux (registered trademark)) on DLD-1 cells
FIG. 5 Tumor growth inhibitory effect of an anti-EGFR antibody (Erbitux (registered trademark)) after treating with miR-143 derivatives
FIG. 6 Expression analysis of proteins controlled by miR143 and proteins of RAS cascade downstream
FIG. 7 Expression analysis of KRAS gene after treating with miR-143 derivatives
FIG. 8 Explanation for designing two kinds of siRNAs against KRAS gene. KRAS has two kinds of isoforms (KRASa and KRASb) and the expression of KRASb is more than KRASa (Above). The target of siR-KRASa is an exon 4a of a KRASa isoform and the target of siR-KRAS is a 3'-untranslated region which is common for two isoforms.
FIG. 9 (Above) Expression analysis of KRAS protein after treating with siRNA whose target is KRAS and (Below) tumor growth inhibitory effect of Erbitux (registered trademark) after treating with siRNA
FIG. 10 Tumor growth inhibitory effect of miR-143 derivatives on DLD-1 cells
FIG. 11 Tumor growth inhibitory effect of miR-143 derivatives in vivo

EMBODIMENTS FOR CARRYING OUT THE INVENTION

Terms used herein, unless otherwise indicated, are used in a sense normally used in this field.

In the present invention, a genetic manipulation method which is well known in this field can be used. For example, it is a method described in Molecular Cloning, A Laboratory Manual, Third Edition, Cold Spring Harbor Laboratory Press (2001) or Current Protocols in Molecular Biology, John Wiley & Sons (2003).

Terms used in this description are explained below. Each term, unless otherwise indicated, has the same meaning when it is used alone or together with other terms.

A miR-143 is a well-known microRNA. A wild-type human miR-143 is, for example, a single-stranded RNA consisting of a sequence of SEQ ID NO: 1 (5'-GGU GCAGUGCUGCAUCUCUGGU-3') (MIMAT0004599, hsa-miR-143-5p) or SEQ ID NO: 2 (5'-UGAGA UGAAGCACUGUAGCUC-3') (MIMAT0000435, hsa-miR-143-3p), and a double-stranded RNA consisting of a sequence of SEQ ID NO: 1 and a sequence of SEQ ID NO: 2.

A "nucleoside" means a compound that a nucleic-acid base and a sugar are bonded by an N-glycoside bond.

An "oligonucleotide" means nucleotides that some of same or different kinds of nucleotide are bonded.

In this description, a "DNA nucleoside" or "RNA nucleoside" means a natural DNA nucleoside or natural RNA nucleoside, and a part of a nucleotide, which is 1 unit for a component of an oligonucleotide. A "natural DNA nucleoside" is as below.

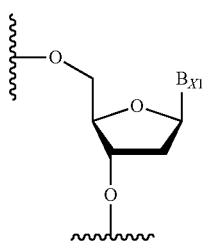

wherein B$_{X1}$ (a nucleic-acid base) is adenine, guanine, cytosine or thymine.

A "natural RNA nucleoside" is as below.

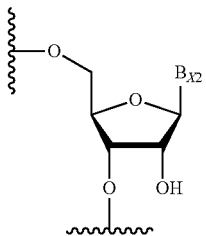

wherein B$_{X2}$ (a nucleic-acid base) is adenine, guanine, cytosine or uracil.

An "RNA oligonucleotide" means an oligonucleotide that some RNA nucleosides are bounded with internucleoside linkages.

In this description, a "nucleoside derivative" means a nucleoside wherein the nucleic base and/or sugar part of the above DNA nucleoside or RNA nucleoside was artificially modified. Any well-known modification for a nucleoside in this field can be used.

Examples of the well-known modification for a nucleotide and the method for modification in this field are described in the following patent documents. WO98/39352, WO99/014226, WO2000/056748, WO2005/021570, WO2003/068795, WO2011/052436, WO2004/016749, WO2005/083124, WO2007/143315, WO2009/071680, WO2014/112463, WO2014/126229 and the like.

Examples of modification for a nucleic-acid base are 5-methyl cytosine, 5-hydroxymethyl cytosine and 5-propynyl cytosine.

Also, a "nucleoside derivative" includes a derivative deleted a nucleic-acid base (Abasic) shown as the formula:

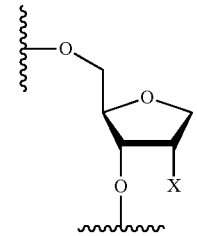

wherein X is hydrogen or OH.

An example of modification for a sugar part is a substituent at the 2' position of a sugar moiety. Examples are 2'-F, 2'-OCH$_3$ (2'-OMe) and 2'-OCH$_2$CH$_2$OCH$_3$ (2'-MOE).

The other example is the following bridged structure between the 4' and 2' positions of a sugar moiety.

4'-(CR$^1$R$^2$)m-O-2',4'-(CR$^1$R$^2$)m-S-2',4'-(CR$^1$R$^2$)m-O—C(=O)-2',4'-(CR$^1$R$^2$)m-NR$^3$-O—(CR$^1$R$^2$)m$_1$-2',4'-(CR$^1$R$^2$)m$_1$-C(=O)—NR$^3$-2',4'-(CR$^1$R$^2$)m$_2$-C(=O)—NR$^3$—Y$^4$-2', 4'-(CH$^1$R$^2$)m$_1$-SO$_2$—NR$^3$-2',4'-(CR$^1$R$^2$)m-NR$^3$-2' or

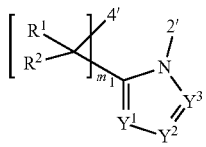

wherein
Y$^4$ is O, S, NH or CH$_2$,
R$^1$ is each independently, a hydrogen atom, halogen, cyano, substituted or unsubstituted alkyl, substituted or unsubstituted alkenyl or substituted or unsubstituted alkynyl,
R$^2$ is each independently, a hydrogen atom, halogen, cyano, substituted or unsubstituted alkyl, substituted or unsubstituted alkenyl or substituted or unsubstituted alkynyl,
R$^3$ is a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalky, substituted or unsubstituted non-aromatic carbocyclylalky, substituted or unsubstituted aromatic heterocyclylalkyl or substituted or unsubstituted non-aromatic heterocyclylalkyl,
Y$^1$ is CR$^4$ or N,
Y$^2$ is CR$^5$ or N,
Y$^3$ is CR$^6$ or N,
R$^4$, R$^5$ and R$^6$ are each independently, a hydrogen atom, halogen, cyano, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl,
m is an integer of 1 to 4,
m$_1$ is an integer of 0 to 3, and
m$_2$ is 0 or 1.

R$^1$ and R$^2$ is preferably a hydrogen atom.

R$^3$ is preferably a hydrogen atom, alkyl, alkenyl, alkynyl, aromatic carbocyclyl, non-aromatic carbocyclyl, aromatic heterocyclyl, non-aromatic heterocyclyl, aromatic carbocyclylalky, non-aromatic carbocyclylalky, aromatic heterocyclylalkyl or non-aromatic heterocyclylalkyl, and may have any one or more substituent(s) selected from Group α.

Group α: a hydroxyl group, alkyl, alkyloxy, mercapto, alkylthio, amino, alkylamino and halogen.

The bridged structure is preferably 4'-(CR$^1$R$^2$)m-O-2' or 4'-(CR$^1$R$^2$)m$_1$—C(=O)—NR$^3$-2' (AmNA, Bridged nucleic acid),
wherein
R$^1$ is each independently, a hydrogen atom, halogen, cyano, substituted or unsubstituted alkyl, substituted or unsubstituted alkenyl, or substituted or unsubstituted alkynyl,
R$^2$ is each independently, a hydrogen atom, halogen, cyano, substituted or unsubstituted alkyl, substituted or unsubstituted alkenyl, or substituted or unsubstituted alkynyl,
R$^3$ is a hydrogen atom, substituted or unsubstituted alkyl, substituted or unsubstituted alkenyl, or substituted or unsubstituted alkynyl,
m is an integer of 1 to 4, and
m$_1$ is an integer of 0 to 2.

The bridged structure is more preferably 4'-(CH$_2$)m-O-2', wherein m is an integer of 1 to 4, or 4'-C(=O)—NR$^3$-2', wherein R$^3$ is a hydrogen atom or alkyl.

4'-(CH$_2$)m-O-2', wherein m is an integer of 1 to 4, is more preferably 4'-CH$_2$-O-2' (LNA, Locked nucleic acid).

Examples and the methods for preparation are described in WO98/39352, WO2003/068795, WO2005/021570 or the like.

4'-C(=O)—NR³-2', wherein R³ is a hydrogen atom or alkyl, is more preferably 4'-C(=O)—NCH₃-2'. Examples and the methods for preparation are described in WO2011/052436.

In addition, a "nucleoside derivative" having a modification in a sugar part includes a group of a ring opened sugar moiety shown as the formula:

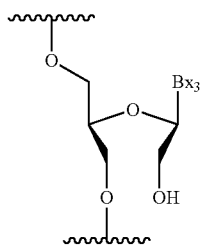

wherein $B_{X_3}$ is an optionally modified nucleic-acid base. Furthermore, 2',5'-RNA (Biochemistry 1998, 37, 7478-7486) is also included.

"Halogen" includes a fluorine atom, a chlorine atom, a bromine atom and an iodine atom. A fluorine atom and a chlorine atom are especially preferable.

"Alkyl" includes a C1 to C15, preferably a C1 to C10, more preferably a C1 to C6 and even more preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

A preferred embodiment of "alkenyl" is vinyl, allyl, propenyl, isopropenyl or butenyl.

"Alkynyl" includes a C2 to C10, preferably a C2 to C8, more preferably a C2 to C6 and further preferably a C2 to C4 linear or branched hydrocarbon group having one or more triple bond(s) at any position(s). Examples include ethynyl, propynyl, butynyl, pentynyl, hexynyl, heptynyl, octynyl, nonynyl and decynyl. Furthermore, it may have double bond(s) at any position(s).

A preferred embodiment of "alkynyl" is ethynyl, propynyl, butynyl or pentynyl.

"Alkylamino" includes monoalkylamino and dialkylamino. These two alkyl groups may be the same or different.

"Alkylcarbonylamino", "alkenylcarbonylamino" or "alkynylcarbonylamino" means a group wherein one or two hydrogen atoms attached to a nitrogen atom of an amino group are replaced with one or two alkylcarbonyl, alkenylcarbony or alkynylcarbony. The two alkylcarbonyl groups, alkenylcarbonyl groups or alkynylcarbonyl groups may be the same or different.

"Alkylcarbamoyl", "alkenylcarbamoyl" or "alkynylcarbamoyl" means a group wherein one or two hydrogen atoms attached to a nitrogen atom of a carbamoyl group are replaced with one or two alkyl, alkenyl or alkynyl. These two alkyl groups, alkenyl groups or alkynyl groups may be the same or different.

Examples of the substituents for "substituted or unsubstituted alkyl", "substituted or unsubstituted alkenyl", "substituted or unsubstituted alkynyl", "substituted or unsubstituted alkyloxy", "substituted or unsubstituted alkylcarbonylamino", "substituted or unsubstituted alkenylcarbonylamino", "substituted or unsubstituted alkynylcarbonylamino", "substituted or unsubstituted alkylcarbamoyl", "substituted or unsubstituted alkenylcarbamoyl " or "substituted or unsubstituted alkynylcarbamoyl" include the following substituents. A carbon atom at any position(s) may be bonded to one or more group(s) selected from the following substituents.

Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyoxy, non-aromatic carbocyclylalkyoxy, aromatic heterocyclylalkyloxy, non-aromatic heterocyclylalkyloxy, aromatic carbocyclylalkyoxycarbonyl, non-aromatic carbocyclylalkyoxycarbonyl, aromatic heterocyclylalkyloxycarbonyl, non-aromatic heterocyclylalkyloxycarbonyl, aromatic carbocyclylalkyamino, non-aromatic carbocyclylalkyamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl and non-aromatic heterocyclylsulfonyl. Furthermore, the substituent may have one or more substituent(s) selected from the above Group α.

"Aromatic carbocyclyl" means a cyclic aromatic hydrocarbon group which is monocyclic or polycyclic having two or more rings. Examples include phenyl, naphthyl, anthryl and phenanthryl.

A preferred embodiment of "aromatic carbocyclyl" is phenyl.

"Non-aromatic carbocyclyl" means a cyclic saturated hydrocarbon group or cyclic unsaturated non-aromatic hydrocarbon group, which is monocyclic or polycyclic having two or more rings. Examples of the non-aromatic carbocyclyl, which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge and a group to form a spiro ring as follows:

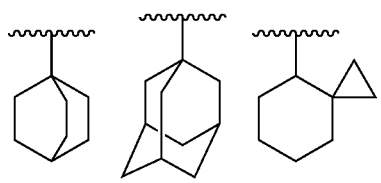

The non-aromatic carbocyclyl, which is monocyclic, is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl and cyclohexadienyl.

Examples of non-aromatic carbocyclyl, which is polycyclic having two or more rings, include indanyl, indenyl, acenaphthyl, tetrahydronaphthyl and fluorenyl.

"Aromatic heterocyclyl" means an aromatic cyclyl, which is monocyclic or polycyclic having two or more rings, containing one or more of heteroatom(s) selected independently from O, S and N.

Examples of aromatic heterocyclyl, which is polycyclic having two or more rings, include a fused ring group wherein an aromatic heterocyclyl, which is monocyclic or polycyclic having two or more rings, is fused with a ring of the above "aromatic carbocyclyl" and/or "non-aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl and thiadiazolyl.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl and thiazolopyridyl.

Examples of aromatic heterocyclyl, which is polycyclic having three or more rings, include carbazolyl, acridinyl, xanthenyl, phenothiazinyl, phenoxathiinyl, phenoxazinyl and dibenzofuryl.

"Non-aromatic heterocyclyl" means a non-aromatic cyclyl, which is monocyclic or polycyclic having two or more rings, containing one or more heteroatom(s) selected independently from O, S and N.

Examples of non-aromatic heterocyclyl, which is polycyclic having two or more rings, include a fused ring group wherein a non-aromatic heterocycle, which is monocyclic or polycyclic having two or more rings, is fused with a ring of "aromatic carbocyclyl", "non-aromatic carbocyclyl" and/or "aromatic heterocyclyl".

In addition, examples of the "non-aromatic heterocyclyl" also include a group having a bridge and a group to form a spiro ring as follows:

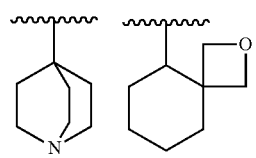

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl and thiazinyl.

Examples of non-aromatic heterocyclyl, which is polycyclic having two or more rings, include indolinyl, isoindolinyl, chromanyl and isochromanyl.

Examples of the substituents on the ring of "aromatic carbocyclyl", "non-aromatic carbocyclyl", "aromatic heterocyclyl" or "non-aromatic heterocyclyl" of "substituted or unsubstituted aromatic carbocyclyl", "substituted or unsubstituted non-aromatic carbocyclyl", "substituted or unsubstituted aromatic heterocyclyl" and "substituted or unsubstituted non-aromatic heterocyclyl" include the following substituents. An atom at any position(s) on the ring may be bonded to one or more group(s) selected from the following substituents.

Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitro so, azide, hydrazino, ureide, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalky, non-aromatic carbocyclylalky, aromatic heterocyclylalkyl, non-aromatic heterocyclylalkyl, aromatic carbocyclylalkyoxy, non-aromatic carbocyclylalkyoxy, aromatic heterocyclylalkyloxy, non-aromatic heterocyclylalkyloxy, aromatic carbocyclylalkyoxycarbonyl, non-aromatic carbocyclylalkyoxycarbonyl, aromatic heterocyclylalkyloxycarbonyl, non-aromatic heterocyclylalkyloxycarbonyl, aromatic carbocyclylalkyoxyalkyl, non-aromatic carbocyclylalkyoxyalkyl, aromatic heterocyclylalkyloxyalkyl, non-aromatic heterocyclylalkyloxyalkyl, aromatic carbocyclylalkyamino, non-aromatic carbocyclylalkyamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl and non-aromatic heterocyclylsulfonyl. Furthermore, the substituent may have one or more substituent selected from the above Group α.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on a carbon atom are substituted as below.

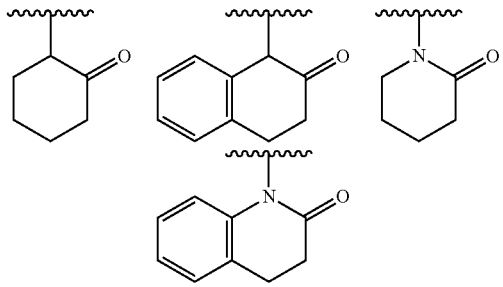

In this description, a "modified internucleoside linkage" means an artificially modified linkage or a linkage without phosphorus atom of phosphodiester (D-oligo) which is an internucleoside linkage of a natural oligonucleotide (a linkage between sugar moieties). Any linkage which is well-known in this field as an internucleoside linkage can be used. Examples of an artificially modified linkage are phosphorothioate (S-oligo), methylphosphonate (M-oligo) and boranophosphate. Furthermore, a linkage described in WO2013/022966, WO2011/005761, WO2014/012081, WO2015/125845 or the like can be used. An example of a linkage without phosphorus atom is a bivalent substituent deriving from non-aromatic carbocyclyl or the like substituted with alkyl, non-aromatic carbocyclyl, haloalkyl or halogen. Example is a bivalent substituent deriving from siloxane, sulfide, sulfoxide, sulfone, acetyl, acetyl formate, acetyl thioformate, acetyl methylene formate, acetyl thioformate, alkenyl, sulfamate, methyleneimino, methylenehydrazino, sulfonate, sulfonamide, amide or the like. In an oligonucleotide, linkages may be same or different. 37 A group of the formula: $dX^1dX^2$, wherein $X^1$ and $X^2$ are each independently A, G, C or T" means a group which two DNA nucleosides bound via an internucleoside linkage. In details, it means the following group.

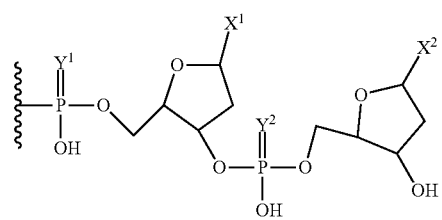

wherein $X^1$ and $X^2$ are each independently adenine, guanine, cytosine or thymine. $Y^1$ and $Y^2$ are each independently O or S.

In this description, a "benzene-pyridine derivative" means the following group.

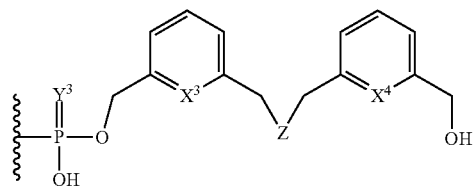

wherein $X^3$ and $X^4$ are each independently N or CH, Z is

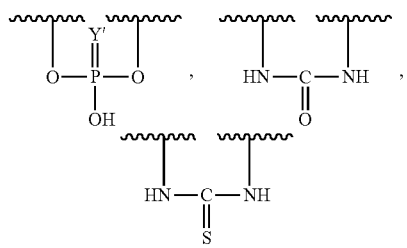

and $Y^3$ and $Y'$ are each independently O or S.

Examples and the methods for preparation are described in Patent Document 1, WO2011/071078 and the like.

Here, the present invention is explained in detail.

The present invention comprises the following "miR-143 derivative (I)".

(I) A microRNA-143 derivative, wherein
the first strand is an oligonucleotide consisting of
a sequence of SEQ ID NO: 3 or
a sequence in which one or two bases are substituted, deleted, inserted or added to the sequence of SEQ ID NO: 3 and
does not include a 3'-end modification, but may include a 5'-end modification; and the second strand is an oligonucleotide consisting of
a sequence of SEQ ID NO: 4 or
a sequence in which one or two bases are substituted, deleted or inserted to the sequence of SEQ ID NO: 4 and
includes a 3'-end modification, and may include a 5'-end modification;
or
a sequence of SEQ ID NO: 5 or
a sequence in which one or two bases are substituted or inserted to the sequence of SEQ ID NO: 5 and
does not include a 3'-end modification, and may include a 5'-end modification;

wherein
the 3'-end modification is a 1 to 5-mer oligonucleotide derivative which may include a nucleoside derivative(s) and/or modified internucleoside linkage(s) or a benzene-pyridine derivative and
the 5'-end modification is a phosphate ester moiety or a group of the formula: =$CQ_1$—P(=O)(OH)$_2$, wherein $Q_1$ is hydrogen, halogen, substituted or unsubstituted alkyl, substituted or unsubstituted alkenyl, substituted or unsubstituted alkynyl, or substituted or unsubstituted alkyloxy.

In addition, the present invention comprises the following "miR-143 derivative (A)".

(A) A microRNA-143 derivative wherein
the first strand is an RNA oligonucleotide wherein the internucleoside linkages are phosphodiester bonds, and
the second strand is an oligonucleotide comprising a nucleoside derivative(s) and/or a modified internucleoside linkage(s),
wherein a group of the formula: $dX^1dX^2$, wherein $X^1$ and $X^2$ are each independently A, G, C or T, or a benzene-pyridine derivative is bound to the 3'-end of the second strand.

The base sequences of the oligonucleotides of miR-143 derivative (A) are not restricted to those of wild-type "miR-143". As long as growth inhibitory effect on cells is maintained, one or several bases in the base sequences of wild-type "miR-143",
wherein an oligonucleotide of the first strand is a sequence of SEQ ID NO: 1 and an oligonucleotide the second strand is a sequence of SEQ ID NO: 2, may be each independently substituted, inserted, deleted and/or added.

The oligonucleotides of the first strand and the second strand of miR-143 derivative (A) are preferably as below.
The first strand is an oligonucleotide less than 30 bases comprising
a sequence of SEQ ID NO: 1 or 3 or
a sequence in which one or several bases are substituted, inserted, deleted and/or added to the sequence of SEQ ID NO: 1 or 3; and
the second strand is an oligonucleotide less than 30 bases comprising
a sequence of SEQ ID NO: 2 or 4 or
a sequence in which one or several bases are substituted, inserted, deleted and/or added to the sequence of SEQ ID NO: 2 or 4.

"one or several base(s)" means one to five, preferably one to three, and more preferably one or two bases.

miR-143 derivative (I) or miR-143 derivative (A) has the activity as miR-143, that is, "growth inhibitory effect on cells" even if the oligonucleotide of the first strand and/or the second strand is "substituted, deleted, inserted or added", "substituted or inserted" or "substituted, inserted, deleted and/or added". The "growth inhibitory effect on cells" can be measured by well-known methods in this field and confirmed. For example, it can be measured by a method described in Example 2 below. When two bases of miR-143 derivative (I) or several bases of miR-143 derivative (A) are mutated, kinds of the mutation, which is substitution, deletion, insertion or addition, may be same or different.

The lengths of the oligonucleotides of the first strand and the second strand of miR-143 derivative (I) or miR-143 derivative (A) may be same or different. The oligonucleotides of the first strand and the second strand of miR-143 derivative (A) are each independently less than 30 bases. For example, they are 15 to 30 bases, 20 to 25 bases, 21 bases, 22 bases, 23 bases, 24 bases or 25 bases.

The oligonucleotides of the first strand and the second strand of miR-143 derivative (I) or miR-143 derivative (A) are especially preferably an oligonucleotide consisting of a sequence of SEQ ID NO: 3 for the first strand and an oligonucleotide consisting of a sequence of SEQ ID NO: 4 for the second strand.

The oligonucleotide(s) of the first strand and/or the second strand of miR-143 derivative (I) may comprise a nucleoside derivative(s) and/or a modified internucleoside linkage(s).

The oligonucleotide of the second strand of miR-143 derivative (A) comprises one or more nucleoside derivative(s) and/or modified internucleoside linkage(s).

The kind, number and position of the nucleoside derivatives comprised in the oligonucleotide(s) of the first strand and/or the second strand of miR-143 derivative (I) or the second strand of miR-143 derivative (A) are not restricted. The kinds of the nucleoside derivatives comprised in the oligonucleotide(s) may be same or different. The nucleoside having a substituent at the 2' position of the sugar moiety are preferably the nucleosides having F, OCH$_3$(OMe) or OCH$_2$CH$_2$OCH$_3$(MOE) at the 2' position of the sugar moiety, and especially preferably the nucleoside having F or OCH$_3$(OMe) at the 2' position of the sugar moiety. The bridged structure between the 4' and 2' positions of a sugar moiety is especially preferably 4'-CH$_2$—O-2'. In addition, the preferable kinds include a group of the formula:

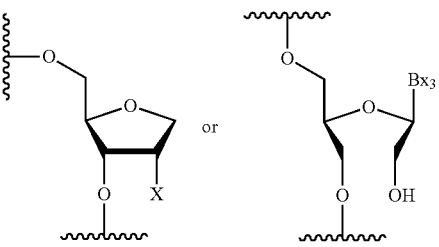

wherein X is hydrogen or OH, and $B_{X_3}$ is optionally modified nucleic-acid base. When "abasic" is used as a nucleotide derivative, the base in the base sequence is deleted because the nucleic-acid base is absent.

The kind, number and position of the modified internucleoside linkages comprised in the oligonucleotide(s) of the first strand and/or the second strand of miR-143 derivative (I) or the second strand of miR-143 derivative (A) are not restricted. The kinds of the modified internucleoside linkages comprised in the oligonucleotide(s) may be same or different. The preferable kind is a phosphorothioate linkage. The preferable number and position is one to several, preferably one to three and more preferably two at the 3'-end and/or 5'-end of each oligonucleotide. Two modified linkages at the 5'-end of the oligonucleotide is especially preferable.

The oligonucleotide of the first strand and the oligonucleotide of the second strand for miR-143 derivative (I) or miR-143 derivative (A) are formed the double-strand. The double-strand with one or several mismatch(es) was included as long as it can be hybridized under a stringent condition.

For example, it is the oligonucleotide of the first strand (sense strand) whose part for hybridization has at least 70% or more, preferably 80% or more, more preferably 90% or more, and most preferably 95% or more homology to a complementary sequence of the oligonucleotide the second strand (antisense strand). The homology shows the similarity as a score, for example, by BLAST, a search program using algorithm discovered by Altschul et al. (The Journal of Molecular Biology, 215, 403-410 (1990).)

A "stringent condition" mean a condition under which a base sequence forms hybrid (so-called specific hybrid) with a specific sequence but any base sequence without the equivalent function does not form hybrid (so-called non-specific hybrid) with the specific sequences. People skilled in this field can easily select the condition by changing a temperature during hybridization reaction or washing, salt concentration in hybridization or washing buffer, or the like. In detail, an example of a stringent condition of the present invention is, but not limited to the condition, which the oligonucleotide is hybridized in 6×SSC (0.9 M NaCl, 0.09 M trisodium citrate) or 6×SSPE (3 M NaCl, 0.2 M $NaH_2PO_4$, 20 mM EDTA.2Na, pH 7.4) at 42° C. and then washed with 0.5×SSC at 42° C. As a hybridization method, well-known methods in this field, for example, southern blot hybridization or the like can be used. In detail, it can be performed according to a method disclosed in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press) or the like.

"One or several mismatch(es)" means one to ten, preferably one to eight, and more preferably one to five mismatch(es).

The double-stranded oligonucleotide of wild-type human miR-143 (SEQ ID NO: 1 and SEQ ID NO: 2) has four mismatched portions. As described in Patent Document 1, the activity can be enhanced by matching at least one to three portion(s) in the sense strand of the mismatched sequence. The number of mismatches in miR-143 derivative (I) is especially preferably three to five including the mismatches of the wild-type human miR-143.

When the oligonucleotide of the second strand of miR-143 derivative (I) is an oligonucleotide consisting of a sequence of SEQ ID NO: 4; or a sequence in which one or two bases are substituted, deleted or inserted to the sequence of SEQ ID NO: 4, a 3'-end modification is included. Here, a "3'-end modification" means a 1 to 5-mer oligonucleotide derivative which may include a nucleoside derivative(s) and/or modified internucleoside linkage(s) or a benzene-pyridine derivative.

The length of an "oligonucleotide derivative" is 1 to 5-mer, preferably 1 to 3-mer and especially preferably 1 or 2-mer.

The kind, number and position of the nucleoside derivatives comprised in an "oligonucleotide derivative" are not restricted. The kinds of the nucleoside derivatives comprised in an oligonucleotide derivative may be same or different. When the nucleoside derivative is the nucleoside having a substituent at the 2' position of the sugar moiety, it is a nucleoside having F, $OCH_3$(OMe) or $OCH_2CH_2OCH_3$ (MOE) at the 2' position of the sugar moiety, and the nucleoside having F or $OCH_3$(OMe) at the 2' position of the sugar moiety is especially preferable. When the nucleoside derivative has the bridged structure between the 4' and 2' positions of a sugar moiety, 4'-$CH_2$—O-2' is especially preferable for the structure. In addition, the preferable kinds include a group of the formula:

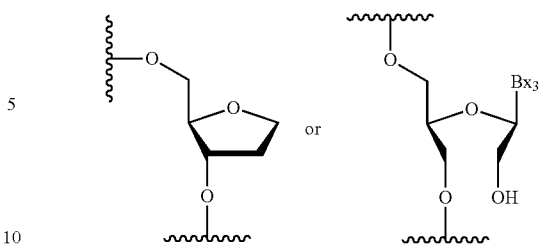

wherein $B_{X_3}$ is an optionally modified nucleic-acid base. When "abasic" is used as a nucleotide derivative, the base in the base sequence is deleted because the nucleic-acid base is absent.

The kind, number and position of the internucleoside linkages comprised in an "oligonucleotide derivative" are not restricted. The kinds of the modified internucleoside linkages comprised in an oligonucleotide derivative may be same or different. The preferable kind is a phosphorothioate linkage. All of the internucleoside linkages comprised in an oligonucleotide derivative are especially preferably phosphorothioate linkages.

An "oligonucleotide derivative" is especially preferably a group of the formula: $dX^1dX^2$, wherein $X^1$ and $X^2$ are each independently an optionally modified nucleic-acid base, as below.

In miR-143 derivative (A), a group of the formula: $dX^1dX^2$, wherein $X^1$ and $X^2$ are each independently A, G, C or T or a benzene-pyridine derivative, is bound to the 3'-end of the oligonucleotide of the second strand.

A group of the formula: $dX^1dX^2$ is preferably a group of

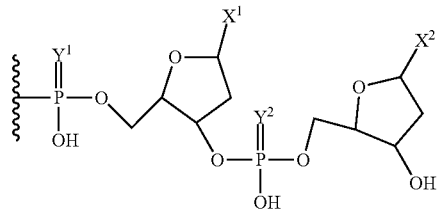

wherein $X^1$ and $X^2$ are each independently adenine, guanine, cytosine or thymine, and $Y^1$ and $Y^2$ are each independently O or S. More preferably, $X^1$ and $X^2$ are thymine (T), and $Y^1$ and $Y^2$ are S.

When a 3'-end modification is included, the modification is bound to the hydroxyl group at the 3'-end of an oligonucleotide. When the modification is an oligonucleotide derivative, the phosphate portion at the 5'-end is bound to the 3'-end of an oligonucleotide as the above formula: $dX^1dX^2$ is bound.

The oligonucleotide(s) of the first strand and/or the second strand of miR-143 derivative (I) may include a 5'-end modification. Here, a "5'-end modification" means a phosphate ester moiety or a group of the formula: $=CQ_1$-P(=O)(OH)$_2$, wherein $Q_1$ is hydrogen, halogen, substituted or unsubstituted alkyl, substituted or unsubstituted alkenyl, substituted or unsubstituted alkynyl, or substituted or unsubstituted alkyloxy.

Furthermore, a phosphate ester moiety may be bound to the 5'-end of the oligonucleotide of the second strand of miR-143 derivative (A).

When the 5'-end modification is a phosphate ester moiety, the phosphate ester moiety is bound to the hydroxyl group at the 5'-end of the oligonucleotide.

When the 5'-end modification is a group of the formula: =CQ$_1$-P(=O)(OH)$_2$, wherein Q$_1$ is hydrogen, halogen, substituted or unsubstituted alkyl, substituted or unsubstituted alkenyl, substituted or unsubstituted alkynyl, or substituted or unsubstituted alkyloxy, it is bound to an oligonucleotide as below. Q$_1$ is preferably hydrogen, halogen, alkyl or alkyloxy, and especially preferably hydrogen or halogen.

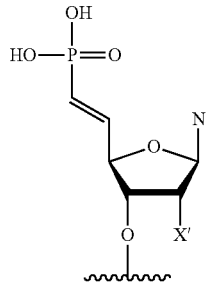

wherein X' is hydrogen, OH, F, OCH$_3$ or OCH$_2$CH$_2$OCH$_3$, and Q$_1$ is hydrogen, halogen, substituted or unsubstituted alkyl, substituted or unsubstituted alkenyl, substituted or unsubstituted alkynyl, or substituted or unsubstituted alkyloxy.

A "phosphate ester moiety" means a phosphate group at the end comprising phosphate ester or modified phosphate ester. In detail, it is a group of the formula: —P(=O)(OH)$_2$ or the modified group. That is, one or more of O or OH is optionally substituted with H, O, OR', S, N(R'), wherein R' is H, an amino-protecting group, or substituted or unsubstituted alkyl, or alkyl. The phosphate ester moiety may comprise substituted or unsubstituted one to three phosphate moiety.

An "amino-protecting group" is not especially restricted as long as a group can stably protect an amino group during nucleic acid synthesis. In details, it is a protecting group which is stable under the acid or neutral condition and can be cleavaged by chemical methods such as hydrogenolysis, hydrolysis, electrolysis and photolysis. Examples are formyl and benzoyl.

The present invention also comprises the following "miR-143 derivative (B)".
(B) A microRNA-143 derivative, wherein
the first strand is an oligonucleotide consisting of a sequence of SEQ ID NO: 3 and
the second strand is an oligonucleotide consisting of a sequence of SEQ ID NO: 5.

The first strand and the second strand are both preferably RNA oligonucleotides. In addition, the internucleoside linkages are preferably phosphodiester bonds.

As a result of study that four mismatched portions in wild-type human miR-143 change to matched pairs, the mismatched number is especially preferably three to five including mismatches of wild-type human miR-143.

Therefore, the following miR-143 derivatives are especially preferable as miR-143 derivatives of the present invention.
(III-1) The microRNA-143 derivative of (I-1), wherein
the first strand is an oligonucleotide consisting of
a sequence in which one base is substituted at position 5, position 7, position 15 or position 22 to the sequence of SEQ ID NO: 3 or
a sequence in which one base is substituted at the position except for position 5, position 7, position 15 and position 22 to the sequence of SEQ ID NO: 3.

If the first strand of the miR-143 derivative of the present invention is an RNA oligonucleotide without any nucleoside derivative and modified internucleoside linkage, tumor growth inhibitory effect for the miR-143 derivative, wherein the second strand is same with SEQ-12 and the first strand has a sequence in which three bases at the 5'-end of the sequence of SEQ ID NO: 3 are deleted, is greatly decreased compared to SEQ-12. That is, when the sense strand is a natural sequence, the length of the sense strand is thought to be important for the activity.

Therefore, the following miR-143 derivatives are especially preferable as miR-143 derivatives of the present invention.
(IV-1) The microRNA-143 derivative of (I-1), wherein
the first strand is an RNA oligonucleotide, which may include a modified internucleoside linkage(s), consisting of
a sequence of SEQ ID NO: 3 or
a sequence in which one or two bases are substituted to the sequence of SEQ ID NO: 3 and
the second strand is an oligonucleotide, which includes a nucleoside derivative(s) and/or modified internucleoside linkage(s)", consisting of a sequence of SEQ ID NO: 4.

In addition, miR-143 derivatives of the present invention have high tumor growth inhibitory effect when all nucleosides of the oligonucleotide in the antisense strand are nucleoside derivatives. Therefore, the following miR-143 derivatives are especially preferable as miR-143 derivatives of the present invention.
(V-1) The microRNA-143 derivative of (I-1), wherein
the first strand is an oligonucleotide, which includes a nucleoside derivative(s) and/or modified internucleoside linkage(s), consisting of
a sequence of SEQ ID NO: 3 or
a sequence in which one or two bases are substituted to the sequence of SEQ ID NO: 3 and
the second strand is an oligonucleotide, in which all nucleosides are nucleoside derivatives and which may include a modified internucleoside linkage(s), consisting of a sequence of SEQ ID NO: 4.

miR-143 derivatives of the present invention have high tumor growth inhibitory effect when the nucleosides having a pyrimidine base in the oligonucleotide are same kinds of nucleoside derivatives and the nucleosides having a purine base are RNA nucleosides. Therefore, the following miR-143 derivatives are especially preferable as miR-143 derivatives of the present invention.
(VI-1) The microRNA-143 derivative of (I-1), wherein
the first strand is an oligonucleotide, wherein includes a modified internucleoside linkage(s), consisting of
a sequence of SEQ ID NO: 3 or
a sequence in which one or two bases are substituted to the sequence of SEQ ID NO: 3 and
the second strand is an oligonucleotide, which may include a modified internucleoside linkage(s), consisting of
a sequence of SEQ ID NO: 4 and
wherein in the oligonucleotides, all nucleosides having a pyrimidine base are same kinds of nucleoside derivatives, and all nucleosides having a purine base are RNA nucleosides.
(VI-2) The microRNA-143 derivative of (VI-1), wherein the nucleoside derivative is a nucleoside having a substituent at the 2' position of the sugar moiety and the substituent is F or OCH$_3$.

miR-143 derivatives of the present invention have high tumor growth inhibitory effect when the modified internucleoside linkages from first to eighth of the 3'-end position comprising a 3'-end modification of the second strand are phosphorothioate linkages. Furthermore, the second strand comprises phosphorothioate linkages as a modified internucleoside linkage at every other position in the oligonucleotide, and then that the second strand has a 5'-end modification. These are thought to be linked to the tumor growth inhibitory effect. Therefore, the following miR-143 derivatives are especially preferable as miR-143 derivatives of the present invention.

(VII-1) The microRNA-143 derivative of (I-1), wherein
the second strand is an oligonucleotide consisting of
a sequence of SEQ ID NO: 4 and
at least one of the modified internucleoside linkages from first to sixth of the 3'-end position of SEQ ID NO: 4 are phosphorothioate linkages.
(VII-2) The microRNA-143 derivative of (VII-1), wherein at least three of the modified internucleoside linkages from first to sixth of the 3'-end position of SEQ ID NO: 4 are phosphorothioate linkages.
(VII-3) The microRNA-143 derivative of (VII-1), wherein all of the modified internucleoside linkages from first to sixth of the 3'-end position of SEQ ID NO: 4 are phosphorothioate linkages.
(VII-4) The microRNA-143 derivative of any one of (VII-1) to (VII-3), wherein an oligonucleotide with modified internucleoside linkages from second to fourteenth of the 5'-end position of SEQ ID NO: 4 comprises one to seven groups of the formula: N'^N'*, wherein N' is a nucleoside, ^ is —P(S)OH— and * is —P(O)OH—, in a row.
(VII-5) The microRNA-143 derivative of (VII-4) comprising seven groups of the formula: N'^N'* in a row.
(VII-6) The microRNA-143 derivative of any one of (VII-1) to (VII-5), wherein the second strand includes a 5'-end modification.

The oligonucleotides of the first and second strands in miR-143 derivatives of the present invention can be synthesized according to the usual methods in this field. For example, they can be easily synthesized by an automated nucleic acid synthesizer which is commercially available (e.g., the synthesizer by Applied Biosystems and Dainippon Seiki). A method for synthesizing is solid-phase synthesis using phosphoramidites, solid-phase synthesis using hydrogen phosphonates or the like. Examples are disclosed in the following Example 1, Tetrahedron Letters 22, 1859-1862 (1981) and the like.

The synthesized first and second strands form a double-stranded oligonucleotide by hybridizing according to the well-known method. Examples are disclosed in the following Example 1.

The present invention encompasses a pharmaceutical composition comprising a miR-143 derivative of the present invention. Any administration method and formulation for the pharmaceutical composition of the present invention can be used if it is a well-known administration method and formulation for miRNA in this field. For example, the administration method and formulation for miRNA are disclosed in the following documents.
Nature Review Drug Discovery, 13, 622-638 (2014)
Patent Document 1, WO2010/050328, WO2011/064130, WO2011/153542, WO2013/163258, WO2013/192486 and the like.

A pharmaceutical composition of the present invention may be administered in a number of ways depending upon whether local or systemic treatment is desired and upon the area to be treated. Examples of an administration method include topical (including ophthalmic, intravaginal, intrarectal, intranasal and transdermal), oral and parenteral. Examples of parenteral administration include intravenous injection or drip, subdermal, intraperitoneal or intramuscular injection, lung administration by aspiration or inhalation, intrathecal administration and intraventricular administration. Intravenous injection or subcutaneous administration is preferable.

When the pharmaceutical composition of the present invention is topically administered, a formulation such as a transdermal patch, ointment, lotion, cream, gel, drop, suppository, spray, liquid and powder can be used.

Examples of the composition for oral administration include powder, granule, suspension or solution dissolved in water or non-aqueous vehicle, capsule, powder and tablet.

Examples of the composition for parenteral, intrathecal or intraventricular administration include sterile aqueous solutions which contain buffers, diluents and other suitable additives.

A pharmaceutical composition of the present invention can be obtained by mixing an effective amount of miR-143 derivatives of the present invention with various pharmaceutical additives suitable for the administration form, such as excipients, binders, moistening agents, disintegrants, lubricants and diluents as needed. When the composition is an injection, it together with a suitable carrier can be sterilized to obtain a composition.

Examples of the excipients include lactose, saccharose, glucose, starch, calcium carbonate and crystalline cellulose.

Examples of the binders include methylcellulose, carboxymethylcellulose, hydroxypropylcellulose, gelatin and polyvinylpyrrolidone.

Examples of the disintegrants include carboxymethylcellulose, sodium carboxymethylcellulose, starch, sodium alginate, agar and sodium lauryl sulfate.

Examples of the lubricants include talc, magnesium stearate and macrogol. Cacao oil, macrogol, methylcellulose or the like may be used as base materials of suppositories.

When the composition is prepared as solutions, emulsified injections or suspended injections, solubilizing agents, suspending agents, emulsifiers, stabilizers, preservatives, isotonic agents and the like which are usually used may be added as needed. For oral administration, sweetening agents, flavors or the like may be added.

To promote the introduction of miR-143 derivatives into the target cells, a pharmaceutical composition of the present invention can comprise a transfection reagent(s). Atelocollagen; liposome; nanoparticle; and cationic lipid such as lipofectin, lipofectamine, DOGS (Transfectam), DOPE, DOTAP, DDAB, DHDEAB, HDEAB, polybrene and poly (ethylenimine) (PEI) can be used as the transfection reagent.

Dosing of a pharmaceutical composition of the present invention is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body. Persons of ordinary skill in the art can easily determine optimal dosages, dosing methodologies and repetition rates. Optimal dosages can be generally calculated based on IC50 or EC50 in vitro or in vivo animal experiments although they change according to relative efficacy of each miR-143 derivatives. Dosages shown as mg/kg are calculated according to the usual method when, for example, a molecular weight of a miR-143 derivative (derived from the sequences and chemical structures of the miR-143 derivative) and the effective dosage such as IC50 (derived from experiments) are provided.

The pharmaceutical compositions of the present invention can be used for preventing or treating the disease related to cell growth because they have growth inhibitory effect on cells. The pharmaceutical compositions of the present invention can be used especially for treating cancer or suppressing the exacerbation thereof. "Cancer" is not especially limited as long as it is a cancer which a human, pet, livestock or the like may contract. It may be solid or invasive cancer, for example, breast cancer, non-small cell lung cancer, gastric cancer, head and neck cancer, esophageal cancer, colorectal cancer, liver cancer, kidney cancer, bladder cancer, endometrial cancer, prostate cancer, angiosarcoma, cervical cancer, brain tumor and germinoma (testicular cancer, ovarian cancer and extragonadal germ cell tumor).

Further growth inhibitory effect can be obtained by combining a miR-143 derivative of the present invention and a well-known antitumor agent.

Examples of a well-known antitumor agent are microtubule targeting agents such as taxanes (e.g., paclitaxel and docetaxel), alkylating agents (e.g., ifosfamide and cyclophosphamide), antimetabolites (e.g., methotrexate and fluorouracil), antitumor antibiotics (e.g., mitomycin C and adriamycin), antitumor antibodies/molecular target agents (e.g., trastuzumab, rituximab, erlotinib, gefitinib, lapatinib, cetuximab, panitumumab and imatinib mesylate) and other antitumor agents (e.g., cisplatin, nivolumab, pembrolizumab and ipilimumab).

When a miR-143 derivative of the present invention is used in combination with a well-known antitumor agent(s), dosing period is not restricted and they can administered to the dosing object at the same time or the different time points. Furthermore, the pharmaceutical composition of a miR-143 derivative of the present invention and a well-known antitumor agent(s) can be administered not only as several formulations comprising each active ingredient(s), but also as a single formulation comprising the both active ingredients. The dosage of a miR-143 derivative of the present invention is not especially restricted as long as it can treat cancer or suppress the exacerbation thereof, and can be determined based on the above "Dosing of a pharmaceutical composition of the present invention". The dosage of a well-known antitumor agent can be determined based on the dosage for administering the antitumor agent in the clinical stages as a single agent. When a miR-143 derivative of the present invention is used in combination, two or more well-known antitumor agents can be used.

As described in the following Example 3, combinations of a miR-143 derivative of the present invention and an EGFR inhibitor are very useful as a medicine for treating KRAS mutant cancer or suppressing the exacerbation thereof.

Examples of the EGFR inhibitor are EGFR tyrosine kinase inhibitors and inhibitors whose target is EGFR extracellular domain. They are preferably anti-EGFR antibodies and more preferably the monoclonal antibodies. Examples are tyrosine kinase inhibitors (e.g. erlotinib, gefitinib and lapatinib) and molecules whose target is EGFR extracellular domain (e.g. cetuximab and panitumumab).

That is, the present invention encompasses "A medicine comprising a combination of a miR-143 derivative of the present invention and an EGFR inhibitor". In detail, it encompasses the above (I-10) to (I-20 and (II-13) to (II-24).

"A pharmaceutical composition comprising a microRNA-143 derivative as an active ingredient to use in combination with an EGFR inhibitor" described in (I-19) and (II-22) encompasses a kit comprising a pharmaceutical composition comprising a miR-143 derivative and a package insert describing how to use in combination with an EGFR inhibitor in a same package.

"A pharmaceutical composition comprising an EGFR inhibitor as an active ingredient to use in combination with a microRNA-143 derivative" described in (I-20) and (II-23) encompasses a kit comprising a pharmaceutical composition comprising an EGFR inhibitor and a package insert describing how to use in combination with a miR-143 derivative in a same package.

EXAMPLE

The present invention will be described in more detail with reference to, but not limited to, the following Examples, Reference Examples and Test Examples.

Example 1 Synthesis of miR143 Derivatives

Solid Phase Synthesis

All oligonucleotides were synthesized using the phosphoramidite method by DNA automatic synthesizer nS-8 (Gene Design Inc.) at the 1 umol scale. A monomer was prepared in 0.1 M acetonitrile solution using RNA amidites having a standard protecting group, 2'F-RNA amidites or 2'OMe-RNA amidites (All amidites were purchased from Proligo Reagents). The coupling time was 5 minutes, and 10 equivalents of the amidite unit were used to condense with one monomer. 0.02 mol/L iodine (tetrahydrofuran/water/pyridinedodine=90.54/9.05/0.41/0.43 (v/v/v/w) were used for PO oxidation. 0.05 mol/L [(dimethylamino-methylidyne) amino]-3H-1,2,4-dithiazoline-3-thion (DDTT) in acetonitrile/pyridine 1/4 (v/v) solution were used for PS oxidation.

Deprotection I (Cleavage from the Resin, and Phosphate Deprotection and Base Deprotection)

For cutting out the oligonucleotides comprising RNA (S-1 to 3, 7, 8 and AS-1 to 3), 28% ammonia solution/methylamine/ethanol=6/1/3 (v/v) was used and the solution was shaken at room temperature for 24 hours. After the resin was washed with 50% ethanol solution, the filtrate was concentrated under reduced pressure, and then lyophilized to obtain white powder.

For cutting out the other oligonucleotides (S-4, 9, 10 and AS-4, 7), 28% ammonia solution/40% methylamine solution/ethanol=7/1/2 (v/v), was used and the solution was shaken at room temperature for 15 hours. After the resin was washed with 50% ethanol water, the filtrate was concentrated under reduced pressure.

Deprotection II (Deprotection of 2'-TBS Group)

To the resulting white powder, N-methylpyrrolidone/triethylamine/triethylamine trihydrofluoride=6/1/2(v/v) was added and the solution was stirred at 65° C. for 1.5 hours. To the reaction mixture was added the same amount of ethoxytrimethylsilane, and the solution was vigorously stirred at room temperature for 10 minutes to obtain the precipitate. After centrifugation at 2500×g (2 minutes), the organic layer was carefully removed. To the resulting precipitate, diethyl ether was added, and the solution was vigorously stirred. Then, in a similar way, the centrifugation was carried out and removed the organic solvent to obtain crude RNA unit (white solid)

Purification

All oligonucleotides were purified by the reversed-phase mode. The purification condition is below.

Mobile phases
Buffer A: 10 mmol/L TEAA (pH 7.0)
Buffer B: acetonitrile
B concentration gradient: 5 to 20% (20 min)
Column: YMC Hydrosphere C18 (20×100 mm) (YMC)
Flow rate: 4 mL/min Each fraction was purified by reversed phase HPLC, the fractions whose purity was 85% or more were collected and concentrated under reduced pressure.

Sequence and Purity Analysis of Oligonucleotides

The resulting oligonucleotides (S-1 to 10 and AS-1 to 7) were confirmed as the target sequences by matching the found molecular weights determined by UPLC/MS measurement and the calculated molecular weights.

Xevo G2 T of System (Waters)
Column: Aquity OST C18 (2.1×50 mm) (Waters)
Mobile phases
Buffer A: 200 mM 1,1,1,3,3,3-hexafluoro-2-propanol/8 mM triethylamine
Buffer B: methanol
B concentration gradient: 10 to 30% (10 min)
Temperature: 50° C.
Flow rate: 0.2 mL/min AS-9 to 23, 27, 28, 31 to 34, 37, 40, 41 and 43 to 57 were also synthesized and confirmed as the target sequences in a similar method from above solid phase synthesis to sequence and purity analysis of oligonucleotides.

The oligonucleotide comprising the VP moiety at the 5'-end (AS-42) was synthesized according to the description in ChemBioChem 2016, 17, 985 to 989 and confirmed as the target sequence in a similar method as above.

S-11 to 26, AS-8, 24 to 26, 29, 30, 35, 36, 38 and 39 were purchased from Gene Design Inc. They were confirmed as the target sequences by matching the found molecular weights determined by MALDI-TOF-MS measurement (autoflex speed, Bruker) and the calculated molecular weights.

Preparation of the Double-Stranded Nucleic Acids

The double-stranded oligonucleotides of SEQ-01 to 21 were prepared as below. After mixing the equimolecular amount of each oligonucleotide, the distilled water was added to make 0.1 mmol/L solution. After still standing at 85° C. for 10 minutes, the solution was naturally cooled to room temperature to obtain the double-stranded nucleic acids. The formation of the double-strand was confirmed by size exclusion chromatography.

Column: YMC-PAC Diol-120 (4.6×300 mm) (YMC)
Mobile phases: 10% acetonitrile in 1× PBS solution
Flow rate: 0.5 mL/min
Temperature: room temperature The double-stranded oligonucleotides of SEQ-22 to 144 were prepared as below. After mixing the equimolecular amount of each oligonucleotide, 1× PBS solution was added to make 0.01 mmol/L solution. After still standing at 95° C. for 5 minutes, the solution was naturally cooled to room temperature to obtain the double-stranded nucleic acids.

As negative controls for assays, Renilla luciferase siRNAs (SEQ-05 and 06) were purchased from Gene Design Inc.

The sequences of the synthesized oligonucleotides are as below. Tables 1 and 2 shows the sense strands (the first strands), Tables 3 to 6 shows the antisense strands (the second strands), and Tables 7 and 8 shows miRNAs.

TABLE 1

| Sense Strand (SEQ ID NO:) | 5' end modification | Oligonucleotide (5'→3') | 3' end modification |
|---|---|---|---|
| S-1 (3) | | U*G*A*G*G*U*G*C*A*G*U*G* C*U*G*C*A*U*C*U*C*U*G*G | |
| S-2 (6) | | U^G^A*G*C*U*A*C*A*G*U* G*C*U*G*C*A*U*C*U*C*U | *dT^dT |
| S-3 (6) | | $U_m$^G^A*G*C*$U_m$*A*$C_m$*A* G*$U_m$*G*$C_m$*$U_m$*G*$C_m$*A* $U_m$*$C_m$*$U_m$*$C_m$*$U_m$ | *dT^dT |
| S-4 (6) | | $U_f$^$G_m$^$A_f$*$G_m$*$C_f$*$U_m$*$A_f$*$C_m$* $A_f$*$G_m$*$U_f$*$G_m$*$C_f$*$U_m$*$G_f$* $C_m$*$A_f$*$U_m$*$C_f$*$U_m$*$C_f$*$U_m$ | *dT^dT |
| S-5 (7) | | U*G*A*G*G*A*G*U*A*G*U*G* A*A*A*G*G*C*C | *dT*dT |
| S-6 (7) | | $U_m$^$G_f$^$A_m$*$G_f$*$G_m$*$A_f$*$G_m$*$U_f$* $A_m$*$G_f$*$U_m$*$G_f$*$A_m$*$A_f$*$A_m$*$G_f$* $G_m$*$C_f$*$C_m$ | *dT^dT |
| S-7 (9) | | U^G^A*G*U*G*C*A*G* U*G*C*U*G*C*A*U*C*U* C*U | *dT^dT |
| S-8 (9) | | $U_m$^G^A*G*G*$U_m$*G*$C_m$*A* G*$U_m$*G*$C_m$*$U_m$*G*$C_m$*A* $U_m$*$C_m$*$U_m$*$C_m$*$U_m$ | *dT^dT |
| S-9 (9) | | $U_f$^$G_m$^$A_f$*$G_m$*$G_f$*$U_m$*$G_f$*$C_m$*$A_f$* $G_m$*$U_f$*$G_m$*$C_f$*$U_m$*$G_f$*$C_m$*$A_f$*$U_m$* $C_f$*$U_m$*$C_f$*$U_m$ | *dT^dT |
| S-10 (3) | | $U_f$^$G_m$^$A_f$*$G_m$*$G_f$*$U_m$*$G_f$* $C_m$*$A_f$*$G_m$*$U_f$*$G_m$*$C_f$*$U_m$* $G_f$*$C_m$*$A_f$*$U_m$*$C_f$*$U_m$*$C_f$* $U_m$*$G_f$*$G_m$ | |
| S-11 (12) | | G*G*U*G*C*A*G*U*G*C*U* C*A*U*C*U*C*U*G*G | |
| S-12 (14) | | U*G*A*G*C*U*G*C*A*G*U*G* C*U*G*C*A*U*C*U*C*U*G*G | |
| S-13 (15) | | U*G*A*G*G*U*A*C*A*G*U*G* C*U*G*C*A*U*C*U*C*U*G*G | |
| S-14 (16) | | U*G*A*G*G*U*G*C*A*G*U*G* C*U*U*C*A*U*C*U*C*U*G*G | |
| S-15 (17) | | U*G*A*G*G*U*G*C*A*G*U*G* C*U*G*C*A*U*C*U*C*A*G*G | |
| S-16 (3) | | U^G^A*G*G*U*G*C*A*G*U* G*C*U*G*C*A*U*C*U*C* U*G*G | |
| S-17 (3) | | $U_f$^$G_m$^$A_f$*$G_m$*$G_f$*$U_f$*$G_f$*$C_f$*$A_f$*$G_m$* $U_f$*$G_m$*$C_f$*$U_f$*$G_m$*$C_f$*$A_f$*$U_f$* $C_f$*$U_f$*$C_f$*$U_f$*$G_m$*G | |
| S-18 (3) | | $U_m$^G^A*G*G*$U_m$*G*$C_m$*A*G* $U_m$*G*$C_m$*$U_m$*G*$C_m$*A*$U_m$* $C_m$*$U_m$*$C_m$*$U_m$*G*G | |
| S-19 (3) | | $U_f$^$G_m$^A*G*G*$U_f$*G*C*A*G* $U_f$*G*C*$U_f$*G*C*A*$U_f$*C* $U_f$*C*$U_f$*G*G | |
| S-20 (19) | | C*G*A*G*G*U*G*C*A*G*U*G* C*U*G*C*A*U*C*U*C*U*G*G | |

TABLE 2

| Sense Strand (SEQ ID NO:) | 5' end modification | Oligonucleotide (5'→3') | 3' end modification |
|---|---|---|---|
| S-21 (3) | | U^$G_m$^$A_m$*$G_m$*$G_m$*U*$G_m$*C*$A_m$*$G_m$*U*$G_m$*C*U*$G_m$*C*$A_m$*U*C*U*C*U*G*G | |
| S-22 (20) | | $T_L$^G^A*G*G*U*G*C*A*G*U*G*C*U*G*C*A*U*C*U*C*U*G*G | |
| S-23 (3) | | UNA(u)^G^A*G*G*U*G*C*A*G*U*G*C*U*G*C*A*U*C*U*C*U*G*G | |
| S-24 (21) | | Ab^G^A*G*G*U*G*C*A*G*U*G*C*U*G*C*A*U*C*U*C*U*G*G | |
| S-25 (3) | | U^G^A*G*G*U*G*C*A*G*U*G*C*U*G*C*A*U*C*U*C*U*C*UNA(u)*G*G | |
| S-26 (22) | | U^G^A*G*G*U*G*C*A*G*U*G*C*U*G*C*A*U*C*U*C*U*C*Ab*G*G | |

TABLE 3

| Antisense Strand (SEQ ID NO:) | 5' end modification | Oligonucleotide (5'→3') | 3' end modification |
|---|---|---|---|
| AS-1 (5) | | U*G*A*G*A*U*G*A*A*G*C*A*C*U*G*U*A*G*C*U*C*A*G*G | |
| AS-2 (4) | | U^G*A*G*A*U*G*A*A*G*C*A*C*U*G*U*A*G*C*U*C*A | ^dT^dT |
| AS-3 (4) | | $U_f$^G^A*G*A*$U_f$*G*A*A*G*$C_f$*A*$C_f$*A*$C_f$*$U_f$*G*$U_f$*A*G*$C_f$*$U_f$*$C_f$*A | ^dT^dT |
| AS-4 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^dT^dT |
| AS-5 (8) | | G*G*C*C*U*U*C*A*C*U*A*C*U*C*C*U*C*A | *dT*dT |
| AS-6 (8) | | $G_f$^$G_m$^$C_f$*$C_m$*$U_f$*$U_m$*$U_f$*$C_m$*$A_f$*$C_m$*$U_f$*$A_m$*$C_f$*$U_m$*$C_f$*$C_m$*$U_f$*$C_m$*$A_f$ | ^dT^dT |
| AS-7 (4) | -P(O)(OH)$_2$ | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^dT^dT |
| AS-8 (2) | | U*G*A*G*A*U*G*A*A*G*C*A*C*U*G*U*A*G*C*U*C | |
| AS-9 (13) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$ | ^dT^dT |
| AS-10 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^dG^dG |

TABLE 4

| Antisense Strand (SEQ ID NO:) | 5' end modification | Oligonucleotide (5'→3') | 3' end modification |
|---|---|---|---|
| AS-11 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$G_f$^$G_m$ |
| AS-12 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$G_m$^$G_m$ |
| AS-13 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$G_f$^$G_f$ |
| AS-14 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$U_m$^$U_m$ |
| AS-15 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$U_f$^$U_f$ |
| AS-16 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$T_L$^$T_L$ |
| AS-17 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | *dT^dT |
| AS-18 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | *dT*dT |
| AS-19 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^dT |
| AS-20 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | *dT |
| AS-21 (4) | | $U_f$*$G_m$*$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | *dT*dT |
| AS-22 (4) | | $U_m$^$G_f$^$A_m$*$G_f$*$A_m$*$U_f$*$G_m$*$A_f$*$A_m$*$G_f$*$C_m$*$A_f$*$C_m$*$U_f$*$G_m$*$U_f$*$A_m$*$G_f$*$C_m$*$U_f$*$C_m$*$A_f$ | ^dT^dT |
| AS-23 (4) | | $U_m$^$G_f$^$A_m$*$G_f$*$A_m$*$U_f$*$G_m$*$A_f$*$A_m$*$G_f$*$C_m$*$A_f$*$C_m$*$U_f$*$G_m$*$U_f$*$A_m$*$G_f$*$C_m$*$U_f$*$C_m$*$A_f$ | ^dT^dT |
| AS-24 (4) | | $U_m$^G^A*G*A*$U_m$*G*A*A*G*$C_m$*A*$C_m$*$U_m$*G*$U_m$*A*G*$C_m$*$U_m$*$C_m$*A | ^dT^dT |
| AS-25 (4) | | $U_f$^$G_f$^A*G*$A_f$*$U_f$*G*$A_f$*$G_f$*C*A*$C_f$*$U_f$*G*U*$A_f$*$G_f$*C*U*$C_f$*$A_f$ | ^dT^dT |
| AS-26 (4) | | $U_m$^$G_m$^A*G*$A_m$*$U_m$*G*A*$A_m$*$G_m$*C*A*$C_m$*$U_m$*G*U*$A_m$*$G_m$*C*U*$C_m$*$A_m$ | ^dT^dT |
| AS-27 (4) | | $U_f$^$G_f$^$A_m$*$G_m$*$A_f$*$U_f$*$G_m$*$A_m$*$A_f$*$G_f$*$C_m$*$A_m$*$C_f$*$U_f$*$G_m$*$U_m$*$A_f$*$G_f$*$C_m$*$U_m$*$C_f$*$A_f$ | ^dT^dT |
| AS-28 (4) | | $U_m$^$G_m$^$A_f$*$G_f$*$A_m$*$U_m$*$G_f$*$A_f$*$A_m$*$G_m$*$C_f$*$A_f$*$C_m$*$U_m$*$G_f$*$U_f$*$A_m$*$G_f$*$C_f$*$U_m$*$C_m$*$A_m$ | ^dT^dT |
| AS-29 (4) | | $U_f$^$G_f$^$A_m$*G*A*U*$G_f$*$A_f$*$A_f$*G*C*A*$C_f$*$U_f$*G*U*A*G*$C_f$*$U_f$*$C_f$*$A_f$ | ^dT^dT |

TABLE 4-continued

| Antisense Strand (SEQ ID NO:) | 5' end modification | Oligonucleotide (5'→3') | 3' end modification |
|---|---|---|---|
| AS-30 (4) | | $U_m$^$G_m$^$A_m$*G*A*U*$G_m$*$A_m$*$A_m$*G*C*A*$C_m$*$U_m$*$G_m$*U*A*G*$C_m$*$U_m$*$C_m$*$A_m$ | ^dT^dT |

TABLE 5

| Antisense Strand (SEQ ID NO:) | 5' end modification | Oligonucleotide (5'→3') | 3' end modification |
|---|---|---|---|
| AS-31 (4) | | $U_f$^$G_f$^$A_f$*$G_m$*$A_m$*$U_m$*$G_f$*$A_f$*$A_f$*$G_m$*$C_m$*$A_m$*$C_f$*$U_f$*$G_f$*$U_m$*$A_m$*$G_m$*$C_f$*$U_f$*$C_f$*$A_f$ | ^dT^dT |
| AS-32 (4) | | $U_m$^$G_m$^$A_m$*$G_f$*$A_f$*$U_f$*$G_m$*$A_m$*$A_m$*$G_f$*$C_f$*$A_f$*$C_m$*$U_m$*$G_m$*$U_f$*$A_f$*$G_f$*$C_m$*$U_m$*$C_m$*$A_m$ | ^dT^dT |
| AS-33 (4) | | $U_f$^$G_m$^$A_m$*$G_m$*$A_f$*$U_m$*$G_f$*$A_m$*$A_m$*$G_m$*$C_f$*$A_m$*$C_f$*$U_m$*$G_f$*$U_m$*$A_f$*$G_m$*$C_f$*$U_m$*$C_f$*$A_m$ | BuP |
| AS-34 (4) | -P(O)(OH)$_2$ | $U_f$^$G_m$^$A_m$*$G_m$*$A_f$*$U_m$*$G_f$*$A_m$*$A_m$*$G_m$*$C_f$*$A_m$*$C_f$*$U_m$*$G_f$*$U_m$*$A_f$*$G_m$*$C_f$*$U_m$*$C_f$*$A_m$ | BuP |
| AS-35 (4) | | $U_f$^G*A*G*A*U*G*A*A*G*$C_f$*A*$C_f$*$U_f$*G*$U_f$*A*G*C*$U_f$*$C_f$*A | ^$U_f$^$U_f$ |
| AS-36 (4) | | $U_f$^G*A*G*A*U*G*A*A*G*C*A*C*$U_f$*G*$U_f$*A*G*C*$U_f$*C*A | ^$U_f$^$U_f$ |
| AS-37 (4) | | U^G*$A_f$*G*$A_f$*U*G*$A_f$*$A_f$*G*C*$A_f$*C*U*G*U*$A_f$*G*C*U*C*$A_f$ | ^dT^dT |
| AS-38 (4) | | $U_m$^G^A*G*A*U*G*A*A*^$U_m$^$U_m$ G*$C_m$*A*$C_m$*$U_m$*G*$U_m$*A*G*C*$C_m$*$U_m$*$C_m$*A | ^$U_m$^$U_m$ |
| AS-39 (4) | | $U_m$^G^A*G*A*U*G*A*A* G*C*A*C*$U_m$*G*$U_m$*A*G*C*$U_m$*C*A | ^$U_m$^$U_m$ |
| AS-40 (4) | | U^$G_m$^$A_m$*$G_m$*$A_m$*U*$G_m$*$A_m$*$A_m$*$G_m$*C*$A_m$*C*U*$G_m$*U*$A_m$*$G_m$*C*U*C*$A_m$ | ^dT^dT |
| AS-41 (4) | | U^G^$A_m$*G*$A_m$*U*G*$A_m$*$A_m$*G*C*$A_m$*C*U*G*U*$A_m$*G*C*U*C*$A_m$ | ^dT^dT |
| AS-42 (4) | VP- | $U_m$^$G_m$^$A_f$*$G_m$*$A_f$*$U_m$*$G_f$*$A_m$*$A_m$*$G_f$*$C_m$*$A_f$*$C_m$*$U_m$*$G_f$*$U_m$*$A_f$*$G_m$*$C_f$*$U_m$*$C_f$*$A_m$ | ^dT^dT |
| AS-43 (4) | | $U_f$^$G_m$^$A_m$*$G_m$*$A_f$*$U_m$*$G_f$*$A_m$*$A_m$*$G_m$*$C_f$*$A_m$*$C_f$*$U_m$*$G_f$*$U_m$*$A_f$*$G_m$*$C_f$*$U_m$*$C_f$*$A_m$ | ^UNA(u)^dT |

TABLE 5-continued

| Antisense Strand (SEQ ID NO:) | 5' end modification | Oligonucleotide (5'→3') | 3' end modification |
|---|---|---|---|
| AS-44 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*UNA(u)*$C_f$*$A_m$ | ^dT^dT |
| AS-45 (4) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^Ab^Ab |

TABLE 6

| Antisense Strand (SEQ ID NO:) | 5' end modification | Oligonucleotide (5'→3') | 3' end modification |
|---|---|---|---|
| AS-46 (2) | | $U_f$^$G_m$^$A_f$*$G_m$*$A_f$*$U_m$*$G_f$*$A_m$*$A_f$*$G_m$*$C_f$*$A_m$*$C_f$*$U_m$*$G_f$*$U_m$*$A_f$*$G_m$*$C_f$*$U_m$*$C_f$*Ab | ^dT^dT |
| AS-47 (18) | | $U_f$^$G_m$^$A_f$*$G_m$*$A_f$*$U_m$*$G_f$*$A_m$*$A_m$*$A_f$*$G_m$*$C_f$*$A_m$*$C_f$*$U_m$*$G_f$*$U_m$*$A_f$*$G_m$*$C_f$*$U_m$*Ab*Ab | ^dT^dT |
| AS-48 (4) | | U^$G_f$*$A_f$*$G_f$*$A_f$*U*$G_f$*$A_f$*$A_f$*$G_f$*C*$A_f$*C*U*$G_f$*U*$A_f$*$G_f$*C*U*C*$A_f$ | ^dT^dT |
| AS-49 (4) | -P(O)(OH)$_2$ | $U_f$^G*A*G*A*U*G*A*A*G* $C_f$*A*$C_f$*$U_f$*G*$U_f$*A*G* $C_f$*$U_f$*$C_f$*A | ^dT^dT |
| AS-50 (4) | -P(O)(OH)$_2$ | $U_f$^$G_m$^$A_f$*$G_m$*$A_f$*$U_m$*$G_f$*$A_m$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^dG^dG |
| AS-51 (4) | -P(O)(OH)$_2$ | $U_f$^$G_m$^$A_f$*$G_m$*$A_f$*$U_m$*$G_f$*$A_m$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$G_m$^$G_m$ |
| AS-52 (4) | -P(O)(OH)$_2$ | $U_f$^$G_m$^$A_f$*$G_m$*$A_f$*$U_m$*$G_f$*$A_m$*$A_m$*$A_f$*$G_m$*$C_f$*$A_m$*$C_f$*$U_m$*$G_f$*$U_m$*$A_f$*$G_m$*$C_f$*$U_m$*$C_f$*$A_m$ | ^$G_f$^$G_f$ |
| AS-53 (4) | -P(O)(OH)$_2$ | $U_m$^G^A*G*A*U*G*A*A* G*$C_m$*A*$C_m$*$U_m$*G*$U_m$*A*G*C*$C_m$*$U_m$*$C_m$*A | ^dT^dT |
| AS-54 (4) | -P(O)(OH)$_2$ | $U_m$^$G_m$^$A_m$*G*A*U*$G_m$*$A_m$*$A_m$*$G_m$*C*A*$C_m$*$U_m$*$G_m$*U*A*G*$C_m$*$U_m$*$C_m$*$A_m$ | ^dT^dT |
| AS-55 (4) | -P(O)(OH)$_2$ | $U_f$^$G_f$^$A_f$*$G_m$*$A_m$*$U_m$*$G_f$*$A_f$*$A_f$*$G_m$*$C_m$*$A_m$*$C_f$*$U_f$*$G_f$*$U_m$*$A_m$*$G_m$*$C_f$*$U_f$*$C_f$*$A_f$ | ^dT^dT |
| AS-56 (18) | -P(O)(OH)$_2$ | $U_f$^$G_m$^$A_f$*$G_m$*$A_f$*$U_m$*$G_f$*$A_m$*$A_m$*$A_f$*$G_m$*$C_f$*$A_m$*$C_f$*$U_m$*$G_f$*$U_m$*$A_f$*$G_m$*$C_f$*$U_m$*Ab*Ab | ^dT^dT |
| AS-57 (4) | -P(O)(OH)$_2$ | $U_m$^$G_f$^$A_m$*$G_f$^$A_f$*$U_f$*$G_m$* $A_f$*$A_m$*$G_f$*$C_m$*$A_m$*$C_m$*$U_f$*$G_m$* $U_f$*$A_m$*$G_f$*$C_m$*$U_f$^ $C_m$^$A_f$ | ^$A_m$^$A_m$ |

TABLE 7

| miRNA | ID |
|---|---|
| SEQ-01 | S-1 |
| | AS-1 |
| SEQ-02 | S-2 |
| | AS-2 |
| SEQ-03 | S-3 |
| | AS-3 |
| SEQ-04 | S-4 |
| | AS-4 |
| SEQ-05 | S-5 |
| | AS-5 |
| SEQ-06 | S-6 |
| | AS-6 |
| SEQ-07 | S-2 |
| | AS-1 |
| SEQ-08 | S-3 |
| | AS-1 |
| SEQ-09 | S-4 |
| | AS-1 |
| SEQ-10 | S-1 |
| | AS-2 |
| SEQ-11 | S-1 |
| | AS-3 |
| SEQ-12 | S-1 |
| | AS-4 |
| SEQ-13 | S-7 |
| | AS-1 |
| SEQ-14 | S-8 |
| | AS-1 |
| SEQ-15 | S-9 |
| | AS-1 |
| SEQ-16 | S-7 |
| | AS-2 |
| SEQ-17 | S-8 |
| | AS-3 |
| SEQ-18 | S-9 |
| | AS-4 |
| SEQ-19 | S-1 |
| | AS-7 |
| SEQ-20 | S-10 |
| | AS-4 |
| SEQ-21 | S-10 |
| | AS-7 |
| SEQ-22 | S-11 |
| | AS-8 |
| SEQ-23 | S-11 |
| | AS-9 |
| SEQ-24 | S-12 |
| | AS-4 |
| SEQ-25 | S-13 |
| | AS-4 |
| SEQ-26 | S-14 |
| | AS-4 |
| SEQ-27 | S-15 |
| | AS-4 |
| SEQ-28 | S-16 |
| | AS-4 |
| SEQ-29 | S-17 |
| | AS-4 |
| SEQ-30 | S-18 |
| | AS-4 |
| SEQ-31 | S-1 |
| | AS-10 |
| SEQ-32 | S-1 |
| | AS-11 |
| SEQ-33 | S-1 |
| | AS-12 |
| SEQ-34 | S-1 |
| | AS-13 |
| SEQ-35 | S-1 |
| | AS-14 |
| SEQ-36 | S-1 |
| | AS-15 |
| SEQ-37 | S-1 |
| | AS-16 |
| SEQ-38 | S-1 |
| | AS-17 |
| SEQ-39 | S-1 |
| | AS-18 |
| SEQ-40 | S-1 |
| | AS-19 |
| SEQ-41 | S-1 |
| | AS-20 |
| SEQ-42 | S-1 |
| | AS-21 |
| SEQ-43 | S-1 |
| | AS-22 |
| SEQ-44 | S-1 |
| | AS-23 |
| SEQ-45 | S-1 |
| | AS-24 |
| SEQ-46 | S-1 |
| | AS-25 |
| SEQ-47 | S-1 |
| | AS-26 |
| SEQ-48 | S-1 |
| | AS-27 |
| SEQ-49 | S-1 |
| | AS-28 |
| SEQ-50 | S-1 |
| | AS-29 |
| SEQ-51 | S-1 |
| | AS-30 |
| SEQ-52 | S-1 |
| | AS-31 |
| SEQ-53 | S-1 |
| | AS-32 |
| SEQ-54 | S-1 |
| | AS-33 |
| SEQ-55 | S-1 |
| | AS-34 |
| SEQ-56 | S-17 |
| | AS-3 |
| SEQ-57 | S-17 |
| | AS-26 |
| SEQ-58 | S-17 |
| | AS-29 |
| SEQ-59 | S-17 |
| | AS-31 |
| SEQ-60 | S-17 |
| | AS-10 |
| SEQ-61 | S-17 |
| | AS-11 |
| SEQ-62 | S-17 |
| | AS-12 |
| SEQ-63 | S-17 |
| | AS-13 |
| SEQ-64 | S-17 |
| | AS-14 |
| SEQ-65 | S-17 |
| | AS-15 |
| SEQ-66 | S-17 |
| | AS-16 |
| SEQ-67 | S-18 |
| | AS-24 |
| SEQ-68 | S-18 |
| | AS-26 |
| SEQ-69 | S-18 |
| | AS-30 |
| SEQ-70 | S-18 |
| | AS-31 |
| SEQ-71 | S-18 |
| | AS-10 |
| SEQ-72 | S-18 |
| | AS-11 |
| SEQ-73 | S-18 |
| | AS-12 |
| SEQ-74 | S-18 |
| | AS-13 |
| SEQ-75 | S-18 |
| | AS-14 |
| SEQ-76 | S-18 |
| | AS-15 |
| SEQ-77 | S-18 |
| | AS-16 |
| SEQ-78 | S-1 |
| | AS-35 |

TABLE 7-continued

| miRNA | ID |
| --- | --- |
| SEQ-79 | S-1 |
|  | AS-36 |
| SEQ-80 | S-1 |
|  | AS-37 |

TABLE 8

| miRNA | ID |
| --- | --- |
| SEQ-81 | S-1 |
|  | AS-38 |
| SEQ-82 | S-1 |
|  | AS-39 |
| SEQ-83 | S-1 |
|  | AS-40 |
| SEQ-84 | S-1 |
|  | AS-41 |
| SEQ-85 | S-17 |
|  | AS-35 |
| SEQ-86 | S-19 |
|  | AS-3 |
| SEQ-87 | S-19 |
|  | AS-35 |
| SEQ-88 | S-18 |
|  | AS-40 |
| SEQ-89 | S-1 |
|  | AS-42 |
| SEQ-90 | S-1 |
|  | AS-43 |
| SEQ-91 | S-1 |
|  | AS-44 |
| SEQ-92 | S-1 |
|  | AS-45 |
| SEQ-93 | S-1 |
|  | AS-46 |
| SEQ-94 | S-1 |
|  | AS-47 |
| SEQ-95 | S-17 |
|  | AS-42 |
| SEQ-96 | S-17 |
|  | AS-43 |
| SEQ-97 | S-17 |
|  | AS-44 |
| SEQ-98 | S-17 |
|  | AS-45 |
| SEQ-99 | S-17 |
|  | AS-46 |
| SEQ-100 | S-17 |
|  | AS-47 |
| SEQ-101 | S-18 |
|  | AS-42 |
| SEQ-102 | S-18 |
|  | AS-43 |
| SEQ-103 | S-18 |
|  | AS-44 |
| SEQ-104 | S-18 |
|  | AS-45 |
| SEQ-105 | S-18 |
|  | AS-46 |
| SEQ-106 | S-18 |
|  | AS-47 |
| SEQ-107 | S-19 |
|  | AS-1 |
| SEQ-108 | S-18 |
|  | AS-1 |
| SEQ-109 | S-1 |
|  | AS-48 |
| SEQ-110 | S-17 |
|  | AS-48 |
| SEQ-111 | S-19 |
|  | AS-48 |
| SEQ-112 | S-20 |
|  | AS-4 |
| SEQ-113 | S-21 |
|  | AS-4 |
| SEQ-114 | S-22 |
|  | AS-4 |
| SEQ-115 | S-23 |
|  | AS-4 |
| SEQ-116 | S-24 |
|  | AS-4 |
| SEQ-117 | S-25 |
|  | AS-4 |
| SEQ-118 | S-26 |
|  | AS-4 |
| SEQ-119 | S-1 |
|  | AS-49 |
| SEQ-120 | S-17 |
|  | AS-7 |
| SEQ-121 | S-18 |
|  | AS-7 |
| SEQ-122 | S-1 |
|  | AS-50 |
| SEQ-123 | S-1 |
|  | AS-51 |
| SEQ-124 | S-1 |
|  | AS-52 |
| SEQ-125 | S-1 |
|  | AS-53 |
| SEQ-126 | S-1 |
|  | AS-54 |
| SEQ-127 | S-1 |
|  | AS-55 |
| SEQ-128 | S-17 |
|  | AS-49 |
| SEQ-129 | S-17 |
|  | AS-55 |
| SEQ-130 | S-17 |
|  | AS-50 |
| SEQ-131 | S-17 |
|  | AS-51 |
| SEQ-132 | S-17 |
|  | AS-52 |
| SEQ-133 | S-18 |
|  | AS-53 |
| SEQ-134 | S-18 |
|  | AS-55 |
| SEQ-135 | S-18 |
|  | AS-50 |
| SEQ-136 | S-18 |
|  | AS-51 |
| SEQ-137 | S-18 |
|  | AS-52 |
| SEQ-138 | S-19 |
|  | AS-49 |
| SEQ-139 | S-1 |
|  | AS-56 |
| SEQ-140 | S-17 |
|  | AS-56 |
| SEQ-141 | S-18 |
|  | AS-56 |
| SEQ-142 | S-1 |
|  | AS-57 |
| SEQ-143 | S-17 |
|  | AS-57 |
| SEQ-144 | S-18 |
|  | AS-57 |

SEQ-01, 10 to 12, 19 to 21, 24 to 144 are miR-143 derivatives of the present invention, and SEQ-02 to 04, 07 to 09, 13 to 18, 22 and 23 are comparative examples. SEQ-05 and 06 are negative controls (Renilla luciferase siRNAs).

In Tables 1 to 6, N (capital letter) is RNA, dN is DNA, Nf is 2'-F RNA, and $N_m$ is 2'-OMe RNA.

^ is —P(S)OH— and * is —P(O)OH—.

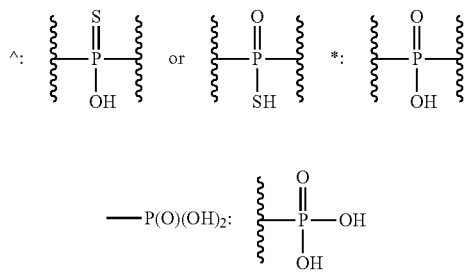

$N_L$, UNA(n) and Ab (Abasic) are the following groups.

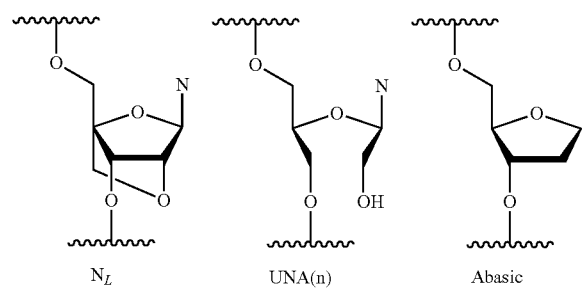

"VP—" at the 5'-end of AS-42 and Um at the end of the oligonucleotides means the following group, and a group of the formula: =CH—P(=O)(OH)$_2$ is the 5'-end modification (VP—).

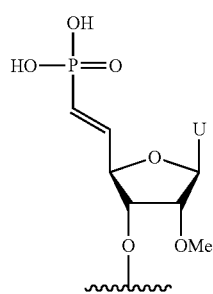

BuP is the following group.

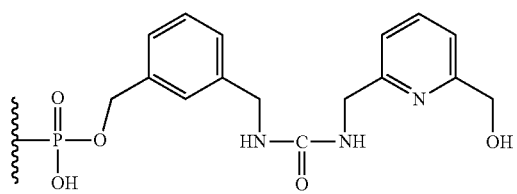 [SMILES: *P(=O)(O)OCc1cccc(CNC(=O)NCc2cccc(CO)n2)c1]

The results of mass spectrometry (the theoretical and found values) of the oligonucleotides are shown below.

TABLE 9

| ID | Molecular weight (Theoretical) | Molecular weight (Found) |
|---|---|---|
| S-1 | 7701.6 | 7698.8 |
| S-2 | 7611.8 | 7611.7 |
| S-3 | 7794.2 | 7790.5 |
| S-4 | 7788.1 | 7786.3 |
| S-7 | 7667.8 | 7669.8 |
| S-8 | 7836.1 | 7838.0 |
| S-9 | 7844.1 | 7841.6 |
| S-10 | 7942.0 | 7941.2 |
| AS-1 | 7755.7 | 7754.4 |
| AS-2 | 7738.0 | 7736.3 |
| AS-3 | 7756.0 | 7757.1 |
| AS-4 | 7914.3 | 7912.6 |
| AS-7 | 7994.1 | 7995.0 |

TABLE 10

| ID | Molecular weight (Theoretical) | Molecular weight (Found) m/z [M − H]− |
|---|---|---|
| S-11 | 6721.0 | 6716.0 |
| S-12 | 7661.5 | 7662.5 |
| S-13 | 7685.6 | 7684.6 |
| S-14 | 7662.5 | 7662.0 |
| S-15 | 7724.6 | 7720.8 |
| S-16 | 7733.7 | 7732.0 |
| S-17 | 7757.7 | 7757.9 |
| S-18 | 7902.1 | 7899.1 |
| S-19 | 7747.7 | 7748.1 |
| S-20 | 7700.6 | 7697.2 |
| S-21 | 7874.0 | 7875.0 |
| S-22 | 7759.7 | 7760.0 |
| S-23 | 7735.7 | 7735.4 |
| S-24 | 7607.6 | 7607.5 |
| S-25 | 7735.7 | 7731.9 |
| S-26 | 7607.6 | 7605.8 |

TABLE 11

| ID | Molecular weight (Theoretical) | Molecular weight (Found) |
|---|---|---|
| AS-9 | 6943.5 | 6944.0 |
| AS-10 | 7964.2 | 7965.0 |
| AS-11 | 8012.1 | 8013.0 |
| AS-12 | 8024.2 | 8025.0 |
| AS-13 | 8000.1 | 8001.0 |
| AS-14 | 7946.1 | 7947.0 |
| AS-15 | 7922.1 | 7922.0 |
| AS-16 | 7970.2 | 7971.0 |
| AS-17 | 7898.1 | 7898.0 |
| AS-18 | 7882.0 | 7882.0 |
| AS-19 | 7593.9 | 7595.0 |
| AS-20 | 7577.8 | 7578.0 |
| AS-21 | 7849.9 | 7851.0 |
| AS-22 | 7914.1 | 7915.0 |
| AS-23 | 7902.1 | 7903.0 |
| AS-27 | 7902.1 | 7902.0 |
| AS-28 | 7926.2 | 7927.0 |
| AS-31 | 7890.1 | 7891.0 |
| AS-32 | 7938.2 | 7939.0 |
| AS-33 | 7636.9 | 7638.0 |
| AS-34 | 7716.9 | 7718.0 |
| AS-37 | 7752.0 | 7752.0 |
| AS-40 | 7920.3 | 7921.0 |
| AS-41 | 7836.2 | 7837.0 |
| AS-42 | 8002.2 | 8003.0 |
| AS-43 | 7918.1 | 7919.0 |
| AS-44 | 7902.1 | 7903.0 |

TABLE 11-continued

| ID | Molecular weight (Theoretical) | Molecular weight (Found) |
|---|---|---|
| AS-45 | 7665.9 | 7667.0 |
| AS-46 | 7750.0 | 7752.0 |
| AS-47 | 7623.9 | 7625.0 |
| AS-48 | 7763.9 | 7765.0 |
| AS-49 | 7835.9 | 7836.0 |
| AS-50 | 8044.1 | 8045.0 |
| AS-51 | 8104.2 | 8104.0 |
| AS-52 | 8080.1 | 8080.0 |
| AS-53 | 7944.2 | 7944.0 |
| AS-54 | 8000.3 | 8001.0 |
| AS-55 | 7970.1 | 7969.0 |
| AS-56 | 7703.9 | 7703.0 |
| AS-57 | 8266.0 | 8265.0 |

TABLE 12

| ID | Molecular weight (Theoretical) | Molecular weight (Found) m/z [M − H]− |
|---|---|---|
| AS-8 | 6736.1 | 6732.2 |
| AS-24 | 7864.2 | 7860.8 |
| AS-25 | 7762.0 | 7759.6 |
| AS-26 | 7906.3 | 7904.6 |
| AS-29 | 7764.0 | 7762.4 |
| AS-30 | 7920.4 | 7922.0 |
| AS-35 | 7763.9 | 7759.1 |
| AS-36 | 7755.9 | 7752.5 |
| AS-38 | 7896.2 | 7893.6 |
| AS-39 | 7840.1 | 7836.8 |

Example 2 Tumor Growth Inhibitory Effect of miR-143 Derivatives

Cell Culture

The human colorectal adenocarcinoma-derived cell line, DLD-1 (KRAS mutant; G13D) was purchased from Japanese Collection Research Bioresources Cell Bank. DLD-1 cells were cultured on Dulbecco's Modified Eagle Medium containing 10% FBS (08456-65; Nacalai Tesque) under the condition of 5% $CO_2$ at 37° C.

The number of viable cells was evaluated by using CellTiter-Glo (registered trademark) Luminescent Cell Viability Assay Kit (G7570; Promega). To each well of a 96-well white plate in which cells were cultured in advance, CellTiter-Glo (registered trademark) Reagent whose amount was equivalent to the amount of the medium was added, and they were stirred in a shaker for 2 minutes to dissolve the cells. After still standing the plates at room temperature for 10 minutes to stable the luminescent signals, the absorbance at 570 nm was measured by luminometer (SpectraMax L MicroPlate Reader, Molecular Devices). The number of viable cells against the control cells (%) was decided as the cell viability.

A Method for Introducing miRNAs into the Cultured Cells

DLD-1 cells were plated with $8 \times 10^3$ cells/well on 96-well white plates. 0.4 μL of Lipofectamine 3000 was added to 4.6 μL of Opti-MEM I medium (Invitrogen), and standed still at room temperature for 5 minutes. In the other tube, 1 μL of 10 μM each miRNA was added to 4 μL of Opti-MEM I medium. The miRNA-Lipofectamine 3000 complexes were prepared by mixing the contents in the both tubes and still standing for 5 minutes. 10 μL/well of the miRNA-Lipofectamine 3000 complexes were added to the cell culture liquid to be 40 nM, and cultured for 72 hours. Then, the number of viable cells was measured.

Tumor Growth Inhibitory Effect of miR-143 Derivatives

After the human colorectal adenocarcinoma-derived cell line, DLD-1 cells were cultured with 40 nM of each miR-143 derivative for 72 hours, the number of remaining viable cells was detected as the luminescent signals by using CellTiter-Glo (registered trademark) Reagent. In FIGS. 1 to 3 and 10, NT (non treatment) means the control cells without introduction of miRNA, and SEQ-05 and 06 are the negative controls.

At first, SEQ-01, which is a miR-143 derivative of the present invention, showed the stronger tumor growth inhibitory effect than SEQ-22 that the sense strand (the first strand) is one base shorter at the 3'-end of and the antisense strand (the second strand) is same compared to the wild type (wild-type human miR-143 consisting of SEQ ID NO: 1 and 2) (FIG. 10). Furthermore, SEQ-01 showed the stronger tumor growth inhibitory effect than SEQ-23 which the oligonucleotide derivative (^dT^dT) was introduced instead of UC at the 3'-end of the antisense strand of SEQ-22 (FIG. 10).

Next, two of four mismatched base pairs in the double strands were matched, and then the oligonucleotide derivatives were introduced at the 3'-end of the both strands (SEQ-02, 03 and 04) to enhance the stability of miR-143. As a result, there was no sequence with stronger tumor growth inhibitory effect than SEQ-01 which the mismatched base pairs were same as the wild type and the nucleoside derivative was not included (FIG. 1).

Next, as a result of consideration that the antisense strand has phosphodiester bonds and RNA as same as the wild type and the oligonucleotide derivative is introduced at the 3'-end of the sense strand, there was no sequence with tumor growth inhibitory effect (FIG. 2, SEQ-07 to 09 and FIG. 3, SEQ-13 to 15). SEQ-07 to 09 are the sequences two of four mismatched base pairs in the double strands were matched, and SEQ-13 to 15 are the sequences with four mismatches as same as the wild type.

On the other hand, as a result of consideration that the sense strand has phosphodiester bonds and RNA as same as the wild type and the nucleoside derivative is introduced at the 3'-end of the antisense strand, the tumor growth inhibitory effect was enhanced compared to SEQ-01 (FIG. 2, SEQ-10 to 12). Especially, SEQ-12 whose antisense strand was modified with 2'-OMe moiety and 2'-F moiety in a row showed the strong growth inhibitory effect. Furthermore, when the phosphate ester moiety was introduced at the 5'-end of the antisense strand of SEQ-12 as the end modification, the inhibitory effect was more enhanced (FIG. 2, SEQ-19). SEQ-10 to 12 and 19 are sequences with four mismatched base pair as same as the wild type.

As a result of consideration that the nucleoside derivative was introduced at the 3'-end of the antisense strand and the nucleoside derivative(s) and/or modified internucleoside linkage(s) were introduced inside the sequences of the both strands, the tumor growth inhibitory effect which is equal to or greater than SEQ-1 was shown (FIG. 3, SEQ-20 and 21). However, when the oligonucleotide derivative was also introduced at the 3'-end of the sense strand, the tumor growth inhibitory effect lowered (FIG. 3, SEQ-16 to 18). SEQ-16 to 21 were sequences with four mismatched base pair as same as the wild type.

Similarly, SEQ-24 to SEQ-143 showed the stronger tumor growth inhibitory effect than SEQ-1. The results of the miR-143 derivatives with especially strong activity are shown below.

TABLE 13

| No. | DLD-1 cell viability (% of NT) at 40 nM | SD |
| --- | --- | --- |
| SEQ-01 | 79.3 | 1.5 |
| SEQ-12 | 63.6 | 7.4 |
| SEQ-19 | 36.7 | 3.5 |
| SEQ-29 | 52.3 | 0.2 |
| SEQ-51 | 46.0 | 4.3 |
| SEQ-52 | 42.3 | 2.2 |
| SEQ-56 | 59.4 | 11.6 |
| SEQ-60 | 51.6 | 6.0 |
| SEQ-73 | 57.2 | 2.7 |
| SEQ-74 | 54.6 | 4.9 |
| SEQ-86 | 56.9 | 1.7 |
| SEQ-89 | 33.9 | 3.8 |
| SEQ-94 | 42.2 | 3.1 |
| SEQ-106 | 37.1 | 0.6 |
| SEQ-122 | 31.0 | 3.9 |
| SEQ-123 | 36.0 | 5.1 |
| SEQ-124 | 36.2 | 1.4 |
| SEQ-127 | 39.2 | 2.0 |
| SEQ-139 | 29.6 | 2.2 |
| SEQ-140 | 39.3 | 3.8 |
| SEQ-141 | 28.4 | 2.3 |
| SEQ-142 | 13.7 | 3.3 |
| SEQ-143 | 13.7 | 2.3 |
| SEQ-144 | 22.1 | 2.6 |

As the above result, in the sequences of the miR-143 derivatives, 3'-end of the first strand has lower permissiveness for the chemical modifications (oligonucleotide derivatives). On the other hand, the tumor growth inhibitory effect can be enhanced by introducing the oligonucleotide derivative or a benzene-pyridine derivative at the 3'-end of the second strand. In addition, the tumor growth inhibitory effect can be enhanced by introducing a nucleoside derivative(s) and/or modified internucleoside linkage(s) inside the sequence or the phosphate ester moiety or a group of the formula: $=CQ_1\text{-}P(=O)(OH)_2$, wherein $Q_1$ is hydrogen, halogen, substituted or unsubstituted alkyl, substituted or unsubstituted alkenyl, substituted or unsubstituted alkynyl, or substituted or unsubstituted alkyloxy, at the 5'-end of the antisense strand.

Example 3 Enhancement of the Tumor Growth Inhibitory Effect by Combining an Anti-EGFR Antibody (Erbitux (Registered Trademark)) and a miR-143 Derivative Cell Culture The human colorectal adenocarcinoma-derived cell line, DLD-1 (KRAS mutant; G13D) was purchased from Japanese Collection Research Bioresources Cell Bank. The cells within 6 months after purchasing or the cells controlled by MycoAlert Mycoplasma Detection Kit (LT07-118; Lonza) were used. DLD-1 cells were cultured on RPMI-1640 medium containing 10% FBS (189-02025; Invitrogen) under the condition of 5% $CO_2$ at 37° C.

The number of viable cells was evaluated by treating with trypsin and the trypan blue-exclusion test. The cell solution after the culture was mixed with the same amount of trypan blue, and the number of viable cells was counted with hemocytometer. The number of viable cells against the control cells (%) was decided as the cell viability.

Gene Transfection Experiment

Each cell was plated with $0.5 \times 10^5$ cells/mL on 6-well plates. DLD-1 cells were plated 24 hours before transfection to be adhered on the plate. As a control, negative miRNA was purchased from Dharmacon. mirVana™ miRNA mimic (hereinafter referred to as "ambion") was purchased from Ambion as the well-known miR-143 derivative. Each miRNA was introduced into the cells by forming a cationic liposome with Lipofectamine RNAiMAX (Invitrogen). Erbitux (registered trademark) (Merck) was administered 48 hours after the transfection and the viable cell count and western blot analysis were carried out 24 hours after the administration.

Combination Effect of an Anti-EGFR Antibody and a miR-143 Derivative

KRAS conveys growth signals from a small-molecule GTP-binding protein, EGFR (epidermal growth factor receptor), to downstream. However, KRAS mutation was confirmed in about 40% of colorectal cancer. Although various anti-EGFR antibodies and EGFR inhibitors have been developed so far, they are said their effects are not enough because of the KRAS mutation. The significant growth inhibitory effect on cells was not confirmed even when Erbitux (registered trademark) was administered for 24 hours in various concentrations in the human colorectal adenocarcinoma-derived cell line, DLD-1 with G13D mutation (FIG. 4). Then, a combination therapy of miR-143 which was reported in Oncogene, 2009, 28 (10), 1385-92; Oncotarget, 5 (14), 5416-27; and the like that it inhibits the expression of Ras protein and an anti-EGFR antibody was considered. The human colorectal adenocarcinoma-derived cell line, DLD-1 cells were cultured with 10 nM of each miR-143 derivative (ambion, SEQ-01 and 12) or negative miRNA (Control) for 48 hours. Then, each concentration of Erbitux (registered trademark) was added and cultured for another 24 hours. The number of remaining viable cells was counted by the trypan blue-exclusion test. As a result, when any miR-143 derivative was not administered (only Erbitux (registered trademark) and Control), growth inhibitory effect on cells against DLD-1 with KRAS mutation was not confirmed. Furthermore, the significant inhibitory effect could not be confirmed even if the well-known miR-143 derivative (ambion) was used. On the other hand, although miR-143 derivatives (SEQ-01 and 12), which the present inventors have intensively studied and found, showed the growth inhibitory effect even if they were individually administered, the concentration dependent enhancement of the effect was confirmed when the dosage of Erbitux (registered trademark) for the combination was increased (FIG. 5). SEQ-12 whose nuclease resistance was enhanced by introducing nucleoside derivatives and modified internucleoside linkages showed the stronger growth inhibitory effect (FIG. 5).

Example 4 Mechanism Analysis for Tumor Growth Inhibition of miR-143 Derivatives Western Blot Analysis 1) Protein Extraction As a protein extraction solution, Protein lysis buffer (10 mM Tris-HCl, 0.1% SDS, 1% NP-40, 0.1% sodium deoxycholate, 150 mM NaCl, 1 mM EDTA) after mixing with 1% Protease inhibitor cocktail, Phosphatase inhibitor cocktail II and III was used. The collected cells were suspended in the protein extraction solution and standed still in the ice for 20 minutes. Then, they were centrifuged at 13,000 rpm at 4° C. for 20 minutes. The supernatant after centrifugation was collected to be protein samples. CelLytic nuclear Extraction Kit (Sigma-Aldrich) was used for fraction extraction of proteins in nuclei and cytoplasm. DC Protein assay kit (Biorad) was used for protein quantification. The quantified proteins were mixed with SDS sample buffer (62.5 mM Tris-HCl, 2% SDS, 10% glycerol, 50 mM DTT and 0.01% bromophenol blue) to be 50 μg/μL. After treating by boiling at 98° C. for 5 minutes, they were standed still on the ice for 5 minutes.

2) Electrophoresis and Transfer

EasySeparator (Wako) and Super Sep Ace (Wako) were used for electrophoresis. After electrophoresis, the gel was soaked in blotting buffer (25 mM Tris, 0.2 M glycine and 20% methanol) for 5 minutes. PVDF membrane (PerkinElmer Life Sciences) was soaked in methanol for 3 minutes and ultrapure water for 5 minutes. Then, it was soaked in blotting buffer for 5 minutes. The filter paper, PVDF membrane, gel and filter paper, which were soaked in the blotting buffer, were piled in turn from the anode side, and transfer was performed at 15 V and 370 mA for 40 minutes.

After the transfer, it was washed with 50 mM Tris-HCl buffer with 0.1% Tween 20 (TBST), soaked in 5% skim milk solution for 1 hour for blocking. It was washed with TBST, soaked in primary antibody diluted with the antibody diluent (2% BSA, 0.01% sodium azide and TBST) and reacted overnight at 4° C. After washing with TBST, it was soaked in secondary antibody diluted with 5% skim milk solution and standed still at room temperature for 1 hour. Then after washing with TBST again, emitting light was performed by Luminata Forte Western HRP Substrate (WBLUF0500; Millipore) and detection was performed by Luminescent image analyzer LAS-4000 UV mini (Fujifilm). Anti-β-actin antibody (A5316; Sigma-Aldrich) was used as a control.

Real-Time PCR

1) RNA Extraction

RNA in cells and tissues were extracted by using NucleoSpin miRNA kit (TaKaRa). The amount of RNA was determined by UV spectrophotometry.

2) Quantification of mRNA

By using PrimeScript RT reagent kit (TaKaRa), reverse transcription of RNA samples was performed at 37° C. for 15 minutes, at 85° C. for 5 seconds and at 4° C. to synthesize cDNA template. Universal SYBR select Master Mix (Applied Biosystems) was used for quantitative reverse transcription-PCR (qRT-PCR) reaction. The amount of GAPDH mRNA was used as an internal control. After early degeneration at 95° C. for 30 seconds, reaction of degeneration at 95° C. for 5 seconds and annealing and elongation reaction at 60° C. for 60 seconds were performed at 40 cycles. Then, melting curves were analyzed in the steps at 95° C. for 15 seconds, 60° C. for 30 seconds and 95° C. for 15 seconds. The reaction of each sample was performed at three times respectively, and the amount of mRNA was calculated by ΔΔCt method.

Antibody

PARP-1 (#9542), LC3B (#3868), Akt (#9272), phospho-Akt (Ser473; #4060), Erk, phospho-Erk and ERK5 used for western blotting were purchased from Cell Signaling Technology. KRAS antibodies were purchased from abeam.

Preparation of siRNA Targeting KRAS

As shown in FIG. 8, KRAS was known as two isoforms, KRASa and KRASb. For KRAS knockdown, siRNAs targeting the two gene sequences whose rank are high in the lists derived from the design software of Invitrogen were purchased. The sequence of the antisense strand of each siRNA is described below, and the sequence of the sense strand is 100% complementary strand of the antisense strand.

(1) siRNA for KRAS (3'UTR region, NM004985.4)

(SEQ ID NO: 10)
5'-AAUGCAUGACAACACUGGAUGACCG (2) siRNA for KRASa (KRASa-specific exon 4a, ORF region, NM033360.3)

(SEQ ID NO: 11)
5'-UAUUGUCGGAUCUCCCUCACCAAUG

Mechanism Analysis of miR-143 Derivatives

The human colorectal adenocarcinoma-derived cell line, DLD-1 cells were cultured with 10 nM each miR-143 derivatives (SEQ-01, 12) for 48 hours, and then for 24 hours after addition of Erbitux (registered trademark) at each concentration. As a result of western blotting, expression of KRAS mRNA and protein were significantly lowered as the target gene, ERK5 (FIGS. 6 and 7). In addition, PI3K/AKT and MAPK (ERK1/2) signals which are downstream growth signals were suppressed. On the other hand, combination effect of siRNA and an anti-EGFR antibody was considered. In two kinds of siRNA purchased from Invitrogen, siR-KRAS designed for 3'UTR (untranslated region) suppressed expression of KRAS protein (FIG. 9, above). When KRAS was knockdown in advance by this siR-KRAS, Erbitux (registered trademark) did not show the significant combination effect. So, tumor growth inhibitory effect of anti-EGFR antibodies were not enhanced only by suppressing KRAS generation with siRNA (FIG. 9, below). The above suggests that the effect of mRNA degradation and translation suppression to the protein of the target gene, KRAS, by miR-143 derivatives of the present invention (SEQ-01 and 12) were remarkably high, and KRAS mRNA level was significantly lowered by silencing several genes relating to generation process of KRAS. As a result, it is thought that EGFR inhibitors (e.g. Erbitux (registered trademark)) act effectively by suppressing the enhanced expression of KRAS.

Example 5 Evaluation of Tumor Growth Inhibition in Animal Models by a miR143 Derivative $3.0 \times 10^6$ cells/100 uL of human proximal tubule cell line with KRAS mutation (Caki-1) were subcutaneously transplanted into the backs of mice. The day of the transplantation was set as Day 0. 50 uL of Opti-MEM solution of the control dsRNA (synthesized by Hokkaido System Science Co., Ltd. (HSS, Sapporo)) or the miR143 derivative of the present invention (SEQ-12) (0.1 nmol/each) was mixed with 2 uL of the cationic liposome reagent (LipoTrust, HSS, Sapporo), and the administration to the mouse tumor on Day 14 after transplantation was initiated. From Day 14 to 23 after transplantation, these mixture were respectively administered from right atrium of mice every 72 hours, and the tumor volumes were measured over time. Tumor volumes were calculated by the following formula. Tumor volume=$0.5236 \times L1 \times (L2)^2$, L1 is major axis and L2 is minor axis. Compared to the mice group administered control double-stranded RNA, the mice groups administered SEQ-12 showed about 44% of tumor growth inhibitory effect (FIG. 11). The sequences of control dsRNA used in this example are below.

(The first strand)

(SEQ ID NO: 23)

5'-GUAGGAGUAGUGAAAGGCC-3'

(The second strand)

(SEQ ID NO: 24)

5'-GGCCUUUCACUACUCCUAC-3'

INDUSTRIAL APPLICABILITY miR-143 derivatives of the present invention show excellent growth inhibitory effect on cells. Furthermore, combinations of a miR-143 derivative of the present invention and an EGFR inhibitor show excellent growth inhibitory effect on cells against KRAS mutant cancer. Therefore, miR-143 derivatives of the present invention are very useful as oligonucleotide therapeutics, especially for treating cancer or suppressing the exacerbation thereof.

---

The invention claimed is:

1. A microRNA-143 derivative, comprising:
a first strand and a second strand,
wherein the microRNA-143 derivative is selected from the group consisting of:
the first strand is SEQ ID NO:3 and the second strand is modified SEQ ID NO:4 $U_f\hat{\ }G_m\hat{\ }A_f*G_m*A_f*U_m*G_f*A_m*A_f*G_m*C_f*A_m*C_f*U_m*G_f*U_m*A_f*G_m*C_f*U_m*C_f*A_m\hat{\ }dT\hat{\ }dT$;
the first strand is SEQ ID NO:3 and the second strand is modified SEQ ID NO:4 —P(O)(OH)$_2$U$_f\hat{\ }$G$_m*$A$_f*$G$_m*$A$_f*$U$_m*$G$_f*$A$_m*$A$_f*$G$_m*$C$_f*$A$_m*$C$_f*$U$_m*$G$_f*$U$_m*$A$_f*$G$_m*$C$_f*$U$_m*$C$_f*$A$_m\hat{\ }$dT$\hat{\ }$dT;
the first strand is modified SEQ ID NO:3 U$_f\hat{\ }$G$\hat{\ }$A*G*G*U$_f*$G*C$_f*$A*G*U$_f$G*C$_f*$U$_f*$G*C$_f*$A*U$_f*$C$_f*$U$_f*$C$_f*$U$_f*$G$\hat{\ }$G and the second strand is modified SEQ ID NO:4 U$_f\hat{\ }$G$_m\hat{\ }$A$_f*$G$_m*$A$_f*$U$_m*$ G$_f*$A$_m*$A$_f*$G$_m*$C$_f*$A$_m*$C$_f*$U$_m*$G$_f*$U$_m*$A$_f*$G$_m*$C$_f*$U$_m*$C$_f*$A$_m\hat{\ }$dT$\hat{\ }$dT;
the first strand is SEQ ID NO:3 and the second strand is modified SEQ ID NO:4 U$_m\hat{\ }$G$_m\hat{\ }$A$_m*$G*A*U*G$_m*$A$_m*$A*G*C*A*C$_m*$U$_m*$G$_m*$U*A*G*C$_m*$U$_m*$C$_m*$A$_m\hat{\ }$dT$\hat{\ }$dT;
the first strand is SEQ ID NO:3 and the second strand is modified SEQ ID NO:4 U$_f\hat{\ }$G$_f$A$_f*$G$_m*$A$_m*$U$_m*$G$_f*$A$_f*$A$_f*$G$_m*$ C$_m*$A$_m*$C$_f*$U$_f*$G$_f*$U$_m*$A$_m*$G$_m*$C$_f*$U$_f*$C$_f*$A$_f\hat{\ }$dT$\hat{\ }$dT;

the first strand is modified SEQ ID NO:3 $U_f\hat{}G\hat{}A$*
$G$*$U_f$*$G$*$C_f$*$A$*$G$*$U_f G$*$C_f$*$U_f$*$G$*$C_f$*$A$*$U_f$*$C_f$*
$U_f$*$C_f$*$U_f$*$G$*$G$ and the second strand is modified SEQ
ID NO:4 $U_f\hat{}G\hat{}A$*$G$*$A$*$U_f$*$G$*$A$*$A$*$G$*$C_f$*$A$*$C_f$*
$U_f$*$G$* $U_f$*$A$*$G$*$C_f$*$U_f$*$C_f$*$A\hat{}dT\hat{}dT$;

the first strand is modified SEQ ID NO:3
$U_f\hat{}G\hat{}A$*$G$*$G$*$U_f$*$G$*$C_f$*$A$*$G$*$U_f G$*$C_f$*$U_f$*$G$*$C_f$*
$A$*$U_f$*$C_f$*$U_f$*$C_f$*$U_f$*$G$*$G$ and the second strand is
modified SEQ ID NO:4 $U_f\hat{}G_m\hat{}A_f$*$G_m$*$A_f$*$U_m$*$G_f$*
$A_m$*$A_f$*$G_m$* $C_f$*$A_m$*$C_f$*$U_m$*$G_f$*$U_m$*$A_f$*$G_m$*$C_f$*$U_m$*
$C_f$*$A_m\hat{}dG\hat{}dG$;

the first strand is modified SEQ ID NO:3
$U_m\hat{}G\hat{}A$*$G$*$G$*$U_m$*$G$*$C_m$*$A$*$G$*$U_m G$*$C_m$*$U_m$*$G$*
$C_m$*$A$*$U_m$*$C_m$*$U_m$*$C_m$*$U_m$*$G$*$G$ and the second
strand is modified SEQ ID NO:4 $U_f\hat{}G_m\hat{}A_f$*$G_m$*$A_f$*
$U_m$*$G_f$*$A_m$*$A_f$*$G_m$*$C_f$*$A_m$* $C_f$*$U_m$*$G_f$*$U_m$*$A_f$*
$G_m$*$C_f$*$U_m$*$C_f$*$A_m\hat{}G_m\hat{}G_m$;

the first strand is modified SEQ ID NO:3
$U_m\hat{}G\hat{}A$*$G$*$G$*$U_m$*$G$*$C_m$*$A$*$G$*$U_m G$*$C_m$*$U_m$*$G$*
$C_m$*$A$*$U_m$*$C_m$*$U_m$*$C_m$*$U_m$*$G$*$G$ and the second
strand is modified SEQ ID NO:4
$U_f\hat{}G_m\hat{}A_f$*$G_m$*$A_f$*$U_m$*$G_f$*$A_m$*$A_f$*$G_m$*$C_f$*$A_m$*
$C_f$*$U_m$*$G_f$*$U_m$*$A_f$*$G_m$*$C_f$*$U_m$*$C_f$*$A_m\hat{}G_f\hat{}G_f$;

the first strand is modified SEQ ID NO:3
$U_f\hat{}G\hat{}A$*$G$*$G$*$U_f$*$G$*$C$*$A$*$G$*$U_f G$*$C$*$U_f$*$G$*$C$*$A$*
$U_f$*$C$*$U_f$*$C$*$U_f$*$G$*$G$ and the second strand is modified
SEQ ID NO:4 $U_f\hat{}G\hat{}A$*$G$*$A$*$U_f$*$G$*$A$*$A$*$G$* $C_f$*$A$*
$C_f$*$U_f$*$G$*$U_f$*$A$*$G$*$C_f$*$U_f$*$C_f$*$A\hat{}dT\hat{}dT$;

the first strand is SEQ ID NO:3 and the second strand is
modified SEQ ID NO:4 $U\hat{}G_m\hat{}A_m$*$G_m$*$A_m$*$U$*
$G_m$*$A_m$*$A_m$*$G_m$* $C$*$A_m$*$C$*$U$*$G_m$*$U$* $A_m$*$G_m$*
$C$*$U$*$C$*$A_m\hat{}dT\hat{}dT$;

the first strand is SEQ ID NO:3 and the second strand is
modified SEQ ID NO:4 $U_f\hat{}G_m\hat{}A_f$*$G_m$*$A_f$*$U_m$*$G_f$*
$A_m$*$A_f$*$G_m$*$C_f$*$A_m$*$C_f$*$U_m$*$G_f$*$U_m$*$A_f$*$G_m$*$C_f$*$U_m$*
$Ab$*$Ab\hat{}dT\hat{}dT$;

the first strand is modified SEQ ID NO:3
$U_m\hat{}G\hat{}A$*$G$*$G$*$U_m$*$G$*$C_m$*$A$*$G$*$U_m G$*$C_m$*$U_m$*$G$*
$C_m$*$A$*$U_m$*$C_m$*$U_m$* $C_m$*$U_m$*$G$*$G$ and the second
strand is modified SEQ ID NO:4
$U_f\hat{}G_m\hat{}A_f$*$G_m$*$A_f$*$U_m$*$G_f$*$A_m$*$A_f$*$G_m$*$C_f$*$A_m$*$C_f$*
$U_m$*$G_f$*$U_m$*$A_f$*$G_m$*$C_f$*$U_m$*$Ab$*$Ab\hat{}dT\hat{}dT$;

the first strand is SEQ ID NO:3 and the second strand is
modified SEQ ID NO:4 —$P(O)(OH)_2U_f\hat{}G_m\hat{}A_f$*
$G_m$*$A_f$*$U_m$*$G_f$*$A_m$*$A_f$*$G_m$*$C_f$*$A_m$*$C_f$*$U_m$*$G_f$*$U_m$*
$A_f$*$G_m C_f$*$U_m$*$C_f$*$A_m\hat{}dG\hat{}dG$;

the first strand is SEQ ID NO:3 and the second strand is
modified SEQ ID NO:4 —$P(O)(OH)_2U_f\hat{}G_m\hat{}A_f$*$G_m$*
$A_f$*$U_m$*$G_f$* $A_m$*$A_f$*$G_m$*$C_f$*$A_m$*$C_f$*$U_m$*$G_f$* $U_m$*
$A_f$*$G_m C_f$*$U_m$*$C_f$*$A_m\hat{}G_m\hat{}G_m$;

the first strand is SEQ ID NO:3 and the second strand is
modified SEQ ID NO:4 —$P(O)(OH)_2U_f\hat{}G_m\hat{}A_f$*
$G_m$*$A_f$*$U_m$*$G_f$*$A_m$*$A_f$*$G_m$*$C_f$*$A_m$*$C_f$*$U_m$*$G_f$*$U_m$*
$A_f$*$G_m C_f$*$U_m$*$C_f$*$A_m\hat{}G_f\hat{}G_f$;

the first strand is SEQ ID NO:3 and the second strand is
modified SEQ ID NO:4 —$P(O)(OH)_2U_f\hat{}G_f\hat{}$
$A_f$*$G_m$*$A_m$*$U_m$*$G_f$*$A_f$*$A_f$*$G_m$* $C_m$*$A_m$*$C_f$*$U_f$* $G_f$*
$U_m$*$A_m$*$G_m$*$C_f$*$U_f$*$C_f$*$A_f\hat{}dG\hat{}dG$;

the first strand is SEQ ID NO:3 and the second strand is
modified SEQ ID NO:4 —$P(O)(OH)_2$
$U_f\hat{}G_m\hat{}A_f$*$G_m$*$A_f$* $U_m$*$G_f$*$A_m$*$A_f$*$G_m$*$C_f$*$A_m$*$C_f$*
$U_m$*$G_f$*$U_m$*$A_f$*$G_m$* $C_f$*$U_m$*$Ab$*$Ab\hat{}dT\hat{}dT$;

the first strand is modified SEQ ID NO:3 $U_f\hat{}G\hat{}A$*$G$*
$G$*$U_f$*$G$*$C_f$*$A$*$G$*$U_f G$*$C_f$*$U_f$*$G$*$C_f$*$A$*$U_f$*$C_f$*$U_f$*
$C_f$*$U_f$*$G$*$G$ and the second strand is modified SEQ ID
NO:4
—$P(O)(OH)_2U_f\hat{}G_m\hat{}A_f$*$G_m$*$A_f$*$U_m$*$G_f$*$A_m$*$A_f$*$G_m$*
$C_f$*$A_m$*$C_f$*$U_m$*$G_f$*$U_m$*$A_f$*$G_m$*$C_f$*$U_m$*$Ab$*$Ab\hat{}dT\hat{}dT$;

the first strand is modified SEQ ID NO:3
$U_m\hat{}G\hat{}A$*$G$*$G$*$U_m$*$G$*$C_m$*$A$*$G$*$U_m G$*
$C_m$*$U_m$*$G$*$C_m$*$A$*$U_m$*$C_m$*$U_m$*$C_m$*$U_m$*$G$*$G$ and the
second strand is modified SEQ ID NO:4
—$P(O(OH)_2U_f\hat{}G_m\hat{}A_f$*$G_m$*$A_f$*$U_m$*$G_f$*$A_m$* $A_f$*$G_m$* $C_f$*
$A_m$*$C_f$*$U_m$*$G_f$*$U_m$*$A_f$* $G_m$*$C_f$*$U_m$*$Ab$*$Ab\hat{}dT\hat{}dT$;

the first strand is SEQ ID NO:3 and the second strand is
modified SEQ ID NO:4 —$P(O)(OH)_2U_m\hat{}G_f\hat{}$
$A_m$*$G_f$*$A_m$*$U_f$*$G_m$*$A_f$*$A_m$*$G_f$*$C_m$*$A_f$*$C_m$*$U_f$*$G_m$*
$U_f$*$A_m$*$G_f$*$C_m$*$U_f$*$C_m$*$A_f A_m\hat{}A_m$;

the first strand is modified SEQ ID NO:3 $U_f\hat{}G\hat{}A$*
$G$*$G$*$U_f$*$G$*$C_f$*$A$*$G$*$U_f G$*$Cf$*$U_f$*$G$*$C_f$*$A$*$U_f$*$C_f$*
$U_f$*$C_f$*$U_f$*$G$*$G$ and the second strand is modified SEQ
ID NO:4
—$P(O)(OH)_2U_m\hat{}G_f\hat{}A_m$*$G_f$*$A_m$*$U_f$*$G_m$*$A_f$* $A_m$*$G_f$*
$C_m$*$A_f$* $C_m$*$U_f$*$G_m$*$U_f$*$A_m$*$G_f$*$C_m$*$U_f$*$C_m$*$A_f A_m\hat{}A_m$;

the first strand is modified SEQ ID NO:3
$U_m G\hat{}A\hat{}$*$G$*$G$*$U_m$*$G$*$C_m$*$A$*$G$*$U_m G$*$C_m$*$U_m$*$G$*
$C_m$*$A$*$U_m$*$C_m$*$U_m$*$C_m$*$U_m$*$G$*$G$ and the second
strand is modified SEQ ID NO:4 —$P(O)(OH)_2$
$U_m\hat{}G_f A_m$*$G_f$*$A_m$*$U_f$*$G_m$*$A_f$*$A_m$*$G_f$*$C_m$*$A_f$*$C_m$*
$U_f$*$G_m$*$U_f$*$A_m$*$G_f$*$C_m$*$U_f$*$C_m$*$A_f\hat{}A_m\hat{}A_m$.

2. A pharmaceutical composition comprising the
microRNA-143 derivative of claim 1.

* * * * *